US009561285B2

(12) United States Patent
Rau et al.

(10) Patent No.: US 9,561,285 B2
(45) Date of Patent: Feb. 7, 2017

(54) CARRIER-LINKED CARBAMATE PRODRUG LINKERS

(75) Inventors: Harald Rau, Dossenheim (DE); Torben Lessmann, Neustadt an der Weinstrasse (DE)

(73) Assignee: Ascendis Pharma AS, Hellerup (DK)

( * ) Notice: Subject to any disclaimer, the term of this patent is extended or adjusted under 35 U.S.C. 154(b) by 1234 days.

(21) Appl. No.: 13/574,120

(22) PCT Filed: Jan. 21, 2011

(86) PCT No.: PCT/EP2011/050819
§ 371 (c)(1),
(2), (4) Date: Oct. 15, 2012

(87) PCT Pub. No.: WO2011/089214
PCT Pub. Date: Jul. 28, 2011

(65) Prior Publication Data
US 2013/0035635 A1    Feb. 7, 2013

(30) Foreign Application Priority Data

Jan. 22, 2010 (EP) .................................. 10151470

(51) Int. Cl.
*A61K 47/48* (2006.01)
(52) U.S. Cl.
CPC ... *A61K 47/48215* (2013.01); *A61K 47/48338* (2013.01)
(58) Field of Classification Search
CPC ................... A61K 47/48215; A61K 47/48338; A61K 47/48784
See application file for complete search history.

(56) References Cited

U.S. PATENT DOCUMENTS

| 6,713,454 | B1* | 3/2004 | Ekwuribe ........ A61K 47/48215 514/25 |
| 7,879,588 | B2 | 2/2011 | Vetter et al. |
| 7,968,085 | B2 | 6/2011 | Hersel et al. |
| 2006/0002890 | A1 | 1/2006 | Hersel et al. |
| 2008/0241102 | A1 | 10/2008 | Hersel et al. |
| 2010/0291021 | A1 | 11/2010 | Vetter et al. |
| 2011/0009315 | A1 | 1/2011 | Hersel et al. |
| 2011/0053848 | A1 | 3/2011 | Cleemann et al. |
| 2011/0112021 | A1 | 5/2011 | Rau et al. |
| 2011/0172390 | A1 | 7/2011 | Vetter et al. |
| 2011/0223230 | A1 | 9/2011 | Hersel et al. |
| 2012/0058084 | A1 | 3/2012 | Rau et al. |
| 2012/0156259 | A1 | 6/2012 | Rau et al. |
| 2012/0156260 | A1 | 6/2012 | Rau et al. |
| 2012/0191039 | A1 | 7/2012 | Rau et al. |

FOREIGN PATENT DOCUMENTS

| EP | 1201649 | 5/2002 |
| WO | WO 01/47562 | 7/2001 |
| WO | WO 2004/019993 | 3/2004 |
| WO | WO 2009/156481 | 12/2009 |

OTHER PUBLICATIONS

Schmidt et al., "Prodrug Mono Therapy: Synthesis and Biological Evaluation of Etoposide Glucuronide-Prodrug," Bioorganic & Medicinal Chemistry 11 (2003) 2277-2283.*
Cheng et al., "Sythesis of Linear, β-Cyclodoxtrin-Based Polymers and Their Camptothecin Conjugates", Bioconjugate Chem, 2003, 1007-1017, 14, American Chemical Society.
Pang et al., "Kinetics of Metabolite Formation and Elimination in the Perfused Rat Liver Preraration; Differences between the Elimination of Preformed Acetaminophen and Acetaminophen Formed from Phenacetin", J. Pharmacol. Exp. Ther., 1978, 178-194, 207, 1, The American Society of Pharmacology and Experimental Therapeutics.
Hussain et al., "Naltrexone-3-salicylate (a Prodrug of Nallrexone): Synthesis and Pharrnacoldnetics in Dogs", Pharmaceutical Research, 1988, 113-115, 5, 2. Plenum Publishing Corporation.
Hussain et al., "Prodrugs for Improved Oral β-Estradiol Bioavailability". Pharmaceutical Research, 1988. 44-47, 5, I, Plenum Publishing Corporation.
Uriz et al., "A new and efficient catalytic method for synthesizing isocyanates from carbamates", Tetrahedron Letters, 2002, 1673-1676, 43, Elsevier Science Ltd.
Broxton, Trevor J., "Trapping of the Intermediate Formed in the $E1c13$ Hydrolysis of Some Alkyl and Aryl $N$(4-Nitrophenyl)calbamates in a Hydroxy Functionalized Micelle", Aust. I. Chem, 1985, 77-83, 38, CSIRO Publishing, Australia.
Mabey et al., "Critical Review of Hydrolysis of Organic Compounds in Water Under Environmental Conditions", J. Phys. Chem. Ref. Data, 1978, 383-415, 7, 2, Stanford Research Institute, Menlo Park, CA, US.
Gomes et al., "Cyclization-activated Prodrugs", Molecules, 2007, 2484-2506, 12, Molecular Diversity Preservation International (MDPI), Basel, Switzerland.
Saari et al., "Cyclization-Activated Prodrugs. Basic Carbamates of 4-Hydroxyanisole", J. of Medicinal Chemistry, 1990, 97-101, 33, American Chemical Society.
Bhatt et al., "Synthesis and in Vivo Antitumor Activity of Poly(L-glutamic acid) Conjugates of 20 ($S$)- Camptothecin", J. Med. Chem., 2003, 190-193, 46, American Chemical Society.

(Continued)

*Primary Examiner* — Paul A Zucker
*Assistant Examiner* — Mark Luderer
(74) *Attorney, Agent, or Firm* — Frommer Lawrence Haug LLP

(57) ABSTRACT

The present invention relates to a prodrug or a pharmaceutically acceptable salt thereof, comprising a drug linker conjugate D-L, wherein D being a biologically active moiety containing an aromatic hydroxyl group is conjugated to one or more polymeric carriers via secondary carbamate-containing linkers L. Such carrier-linked prodrugs achieve drug releases with therapeutically useful half-lives. The invention also relates to pharmaceutical compositions comprising said prodrugs and their use as medicaments.

16 Claims, No Drawings

(56) References Cited

OTHER PUBLICATIONS

Testa et al., Metabolic Hydrolysis and Prodrug Design (Chapter 8: "The Hydrolysis of Carboxylic Acid Ester Prodrugs"), 419-534, Wiley-VCH.
Testa et al., Metabolic Hydrolysis and Prodrug Design, 2003, p. 5, Wiley-VCH.
Product list of JenKem Technology, USA (accessed and downloaded from www.jenkemusa.com on Jul. 28, 2009).
Shabat et al., "Chemical Adaptor Systems", Chem. Eur. J., 2004, 2626-2634, 10, Wiley-VCH Verlag GmbH & Co. KGaA, Weinheim.
Na et al., "Monitoring of peptide acylation inside degrading PLGA microspheres by capillary electrophoresis and MALDI-T of mass spectrometry", Journal of Controlled Release, 2003, 291-299, 92, Elsevier B.V.
Duncan et al., "The Drawing Era of Polymer Therapeutics", Nature Reviews Drug Discovery, 2003, 347-360, 2, Nature Publishing Group.
Caliceti et al., "Pharmacokinetic and biodistribution properties of poly(ethylene glycol)-protein conjugates", Advanced Drug Delivery Reviews, 2003, 1261-1277, 55, Elsevier B.V.
Peleg-Shulman et al., "Reversible PEGylation: A Novel Technology to Release Native Interferon α2 over a Prolonged Time Period", J. Med. Chem., 2004, 4897-4904, 47, American Chemical Society.
Testa et al., Metabolic Hydrolysis and Prodrug Design, 2003, p. 4, Wiley-VCH.
Greenwald et al., "Drug Delivery Systems Employing 1,4- or 1,6-Elimination: Poly(ethylene glycol) Prodrugs of Amine-Containing Compounds", J. Med. Chem., 1999, 3657-3667, 42, American Chemical Society.
Luq et al., "A Hyaluronic Acid-Taxol Antitumor Bioconjugate Targeted to Cancer Cells", Biomacromolecules, 200, 208-218, 1, American Chemical Society.

\* cited by examiner

US 9,561,285 B2

CARRIER-LINKED CARBAMATE PRODRUG LINKERS

The present application claims priority from PCT Patent Application No. PCT/EP2011/050819 filed on Jan. 21, 2011, which claims priority from European Patent Application No. EP 10 151 470.1 filed on Jan. 22, 2010, the disclosures of which are incorporated herein by reference in their entirety.

BACKGROUND OF THE INVENTION

1. Field of the Invention

The present invention is directed to carrier-linked prodrugs having temporary carbamate linkages between amine-containing moieties and phenolic hydroxyl groups of biologically active entities such as peptides, proteins, natural products or synthetic chemical compounds. Such carrier-linked prodrugs are characterized by slow release of unmodified biologically active entity.

It is noted that citation or identification of any document in this application is not an admission that such document is available as prior art to the present invention.

Typically, carriers employed for extended time-action engineering in drug delivery are either used in a non-covalent fashion, with the drug physicochemically formulated into a solvent-carrier mixture, or by permanent covalent attachment of a carrier reagent to one of the drug's functional groups.

Non-covalent drug encapsulation into polymeric carriers has been applied to depot formulations for long-acting release profiles. Typically, the drug is mixed with carrier material and processed in such fashion, that the drug becomes distributed inside the bulk carrier. For instance polymer-drug aggregates may be shaped as microparticles which are administered as an injectable suspension or the polymer-drug aggregates are formulated as gels which are administered in a single bolus injection. Known in the art are also liposomal formulations, where the carrier may be a polymeric or non-polymeric entity capable of solubilizing the drug. Drug release occurs when the carrier swells or physically deteriorates or chemical degradation allows diffusion of the drug to the exterior and subsequently into the biological environment. Such chemical degradation processes may be autohydrolytic or enzyme-catalyzed. An example for a marketed drug based on bolus administration of a drug-polymer gel is Lupron Depot. An example for a marketed drug based on suspended microparticles is Nutropin Depot. An example for a marketed drug based on a liposomal formulation is Doxil.

A disadvantage of the non-covalent approach is that in order to prevent uncontrolled, burst-type release of the drug, encapsulation of the drug has to be highly efficient by creating a sterically highly crowded environment. Restraining the diffusion of an unbound, water soluble drug molecule requires strong van der Waals contacts, frequently mediated through hydrophobic moieties. Many conformationally sensitive drugs, such as proteins or peptides, are rendered dysfunctional during the encapsulation process and/or during subsequent storage of the encapsulated drug. In addition, such amino-containing drugs readily undergo side reactions with carrier degradation products (see, for example, D. H. Lee et al., J. Contr. Rel., 2003, 92, 291-299). Furthermore, dependence of the release mechanism of the drug upon biodegradation may cause interpatient variability.

Alternatively, the drugs may be conjugated to a carrier through permanent covalent bonds. This approach is applied to various classes of molecules, from so-called small molecules, through natural products up to larger proteins.

Liraglutide is an example of a peptide drug that achieves an extended half-life by permanent covalent modification with a palmitoyl moiety. The fatty acid alkyl chain serves to provide albumin binding in vivo and the palmitoylated peptide forms an albumin complex that acts as a drug reservoir in the blood stream.

Albuferon is an example of a protein drug that achieves an extended half-life by permanent covalent modification with another protein that in itself has a long half-life. The corresponding fusion protein of albumin and interferon alpha, Albuferon, exhibits a significantly extended half-life as compared to interferon alpha.

Many small molecule medicinal agents, like alkaloids and anti-tumor agents, show low solubility in aqueous fluids. One way to solubilize these small molecule compounds is to conjugate the small molecule compounds to hydrophilic (water-soluble) polymers. A variety of water-soluble polymers, such as human serum albumin, dextran, lectins, poly (ethylene glycol) (PEG), poly(styrene-co-maleic anhydride), poly(N-hydroxypropylmethacrylamide), poly (divinyl ether-co-maleic anhydride), hyaluronic acid have been described for this purpose (R. Duncan, Nature Rev. Drug Disc., 2003, 2, 347-360).

Covalent modification of biological molecules with poly (ethylene glycol) has been extensively studied since the late 1970s. So-called PEGylated proteins have shown improved therapeutic efficacy by increasing solubility, reducing immunogenicity, and increasing circulation half-live in vivo due to reduced renal clearance and proteolysis by enzymes (see, for example, Caliceti P., Veronese F. M., Adv. Drug Deliv. Rev. 2003, 55, 1261-1277).

However, many biological molecules such as IFNalfa2, saquinavir or somatostatin are inactive or show decreased biological activity when a carrier is covalently conjugated to the drug (T. Peleg-Shulman et al., J. Med. Chem., 2004, 47, 4897-4904).

In order to avoid shortcomings imposed by either the non-covalent polymer mixtures or the permanent covalent attachment, it may be preferable to employ a prodrug approach for chemical conjugation of the drug to the polymer carrier. In such polymeric prodrugs, the biologically active moieties (drugs, therapeutic, biological molecule, etc.) are typically linked to the polymeric carrier moiety by a temporary bond formed between the carrier moiety and a hydroxy, amino or carboxy group of the drug molecule.

Prodrugs are therapeutic agents that are almost inactive per se but are predictably transformed into active molecular entities (see B. Testa, J. M: Mayer in Hydrolysis in Drug and Prodrug Metabolism, Wiley-VCH, 2003, page 4). The carrier prodrug approach may be applied in such a fashion that the drug is released in vivo from the polymer in order to regain its biological activity. The reduced biological activity of the prodrug as compared to the released drug is of advantage if a slow or controlled release of the drug is desired. In this case, a relatively large amount of prodrug may be administered without concomitant side effects and the risk of overdosing. Release of the drug occurs over time, thereby reducing the necessity of repeated and frequent administration of the drug.

Prodrug activation may occur by enzymatic or non-enzymatic cleavage of the temporary bond between the carrier and the drug molecule, or a sequential combination of both, i.e. an enzymatic step followed by a non-enzymatic rearrangement. In an enzyme-free in-vitro environment such as an aqueous buffer solution, a temporary bond such as an ester or amide may undergo hydrolysis, but the corresponding rate of hydrolysis may be much too slow and thus outside the therapeutically useful range. In an in vivo environment, esterases or amidases are typically present and the esterases and amidases may cause significant catalytic acceleration of the kinetics of hydrolysis from twofold up to several orders of magnitude (see, for example, R. B. Greenwald et al. J. Med. Chem. 1999, 42 (18), 3857-3867).

Prodrugs fall in two classes, bioprecursors and carrier-linked prodrugs. Bioprecursors do not contain a carrier group and are activated by the metabolic creation of a functional group. In carrier-linked prodrugs the active substance is linked to a carrier moiety by a temporary linkage. The carrier may be biologically inert, such as, for instance, PEG or may have targeting properties, conferred by antibodies, for example. This invention is concerned with polymeric carrier-linked or macromolecular prodrugs, where the carrier itself is a macromolecule such as a carrier protein or polysaccharide or poly(ethylene glycol).

Cleavage of a carrier prodrug generates a molecular entity (drug) of increased bioactivity and at least one side product, the carrier. After cleavage, the bioactive entity will reveal at least one previously conjugated and thereby protected functional group, and the presence of this group typically contributes to the drug's bioactivity.

In order to implement a prodrug strategy, at least one selected functional group in the drug molecule is employed for attachment of the carrier polymer. Preferred functional groups are hydroxyl or amino groups. Consequently, both the attachment chemistry and hydrolysis conditions depend on the type of functional group employed.

Numerous macromolecular prodrugs are described in the literature where the temporary linkage is a labile ester bond. In these cases, the functional group provided by the bioactive entity is either a hydroxyl group or a carboxylic acid (e.g. Y Luo, M R Ziebell, G D Prestwich, "A Hyaluronic Acid—Taxol Antitumor Bioconjugate Targeted to Cancer Cells", Biomacromolecules 2000, 1, 208-218, J Cheng et al, Synthesis of Linear, beta-Cyclodextrin Based Polymers and Their Camptothecin Conjugates, Bioconjugate Chem. 2003, 14, 1007-1017, R. Bhatt et al, Synthesis and in Vivo Antitumor Activity of Poly(L-glutamic acid) Conjugates of 20(S)-Camptothecin, J. Med. Chem. 2003, 46, 190-193; R. B. Greenwald, A. Pendri, C. D. Conover, H. Zhao, Y. H. Choe, A. Martinez, K. Shum, S. Guan, J. Med. Chem., 1999, 42, 3657-3667; B. Testa, J. M: Mayer in Hydrolysis in Drug and Prodrug Metabolism, Wiley-VCH, 2003, Chapter 8).

Especially for therapeutic biomacromolecules, but also for certain small molecule drugs, it may be desirable to link the carrier to aromatic (phenolic) hydroxyl groups of the bioactive entity.

Drugs containing phenolic hydroxyl groups are known to undergo extensive first-pass metabolism. The rapid inactivation is mainly due to sulfation, glucuronidation and methylation of the phenolic moieties, catalyzed by enzymes in the gut and liver. Therefore, the metabolizable moiety of phenolic drugs has been traditionally masked to yield ester prodrugs. This approach is only useful, if the prodrug-to-drug conversion occurs in an organ other than the intestine or liver. If the enzymatic conversion of the prodrug to the drug occurs in the same organ as the metabolic inactivation, the overall metabolism inactivation of the prodrug is more efficient than that of the parent drug. This phenomenon is described for example for paracetamol and its prodrug phenacetin by Pang & Gillette (J. Pharmacol. Exp. Ther. 207:178, 1978).

In general, protection of a phenolic function in the form of a prodrug requiring enzymatic cleavage may often be ineffective, since the processing may occur before the drug reaches the side of metabolism.

Another major drawback of predominantly enzymatic cleavage is interpatient variability. Enzyme levels may differ significantly between individuals resulting in biological variation of prodrug activation by the enzymatic cleavage. The enzyme levels may also vary depending on the site of administration. For instance, it is known that in the case of subcutaneous injection, certain areas of the body yield more predictable therapeutic effects than others. To reduce this unpredictable effect, non-enzymatic cleavage or intramolecular catalysis is of particular interest (see, for example, B. Testa, J. M: Mayer in Hydrolysis in Drug and Prodrug Metabolism, Wiley-VCH, 2003, page 5).

Furthermore, it is difficult to establish an in vivo-in vitro correlation of the pharmacokinetic properties for enzyme-dependent carrier-linked prodrugs. In the absence of a reliable in vivo-in vitro correlation optimization of a release profile becomes a cumbersome task.

Several non-enzymatically cleavable prodrugs of aromatic hydroxyl group containing drugs have been attempted. Hussain and Shefter (Pharm. Res. 5:113-115) describe ester prodrugs of naltrexone, using salicylate. Similar results were obtained with prodrugs of beta-estradiol (Hussain et al., Pharm. Res. 5: 44-47). The reported half-life of the prodrug was around one hour, indicating rapid turn-over, consequently limiting the usefulness of such prodrugs.

The international application WO-A 2001/47562 describes polymeric prodrugs containing phenolic drug moieties linked to primary amines by means of a hydrolyzable carbamate group. According to the publication, hydrolysis of such prodrugs yielded the degradation products Y—Ar—OH (phenolic drug moiety)+POLY-NH$_2$ (a polymeric carrier carrying a primary amino group) and hydrogencarbonate.

The use of primary amines in the formation of carbamate prodrugs of phenolic drug moieties as in WO-A 2001/47562 raises concerns with respect to the safety of the degradation products. It is well known that hydrolysis of secondary carbamates proceeds through nucleophilic attack of hydroxide at the carbonyl moiety ($B_{AC}2$ mechanism) to form the tetrahedral intermediate that breaks down by loss of alkoxide ion to give the carboxylated amine, which loses $CO_2$ rapidly to give the free amine. On the other hand, hydrolysis of the primary carbamates proceeds through an elimination mechanism (E1cB) involving facile loss of a proton on the carbamate nitrogen and subsequent formation of the isocyanate. Depending on the reaction conditions and structure of the reaction products, such isocyanates may be isolated in good yield. For instance Uriz et al (Tetrahedron Letters 43 (2002) 1673-6) detail an efficient method of synthesizing isocyanates from carbamates. In an aqueous environment, isocyanates typically do not persist but still may be remarkably stable for hours and may—in the presence of other reactive moieties—undergo side reactions. For instance, Broxton (Austr. J. Chem. 38 (1985) 77 ff.) describes how during primary carbamate hydrolysis in micelles, the intermediate p-nitrophenyl isocyanate was trapped by the hydroxyl group of the functional micelle to form a new carbamate directly bound to the detergent molecules of the micelle.

Furthermore, primary carbamates may exhibit hydrolysis rates that are not therapeutically useful. For instance, a carbamate of p-nitrophenyl-O—CO—NH-phenyl was shown to hydrolyze with a half-life of 26 seconds at pH 7 (Mabey, W. and Mill, T., J. Phys. Chem. Ref., Data 7 (1978)

383-415). Due to the limitations imposed by the drug moiety in a corresponding prodrug it may not be possible to slow down a primary carbamate's rate of hydrolysis by several orders of magnitude to achieve release rates compatible with once-daily or once-weekly prodrug administration.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of any previously described product, method of making the product, or process of using the product.

SUMMARY OF THE INVENTION

Therefore, an object of the present invention is to provide carrier-linked prodrug linkers suitable for drugs containing aromatic hydroxyl groups from which free drug is released with therapeutically useful half-lives.

This object is achieved by a prodrug or a pharmaceutically acceptable salt thereof comprising a drug linker conjugate D-L, wherein
D is a biologically active moiety containing an aromatic hydroxyl group; and
L is a non-biologically active linker containing
i) a moiety $L^1$ represented by formula (I),

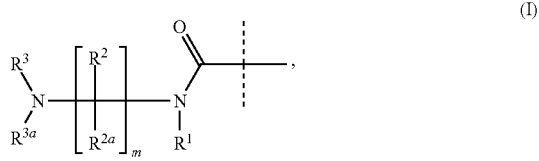

wherein the dashed line indicates the attachment of $L^1$ to the aromatic hydroxyl group of D by forming a carbamate group;
$R^1$ is selected from the group consisting of $C_{1-4}$ alkyl; heteroalkyl; $C_{3-7}$ cycloalkyl; and

$R^2$, $R^{2a}$, $R^3$, $R^{3a}$ are independently selected from hydrogen, substituted or non-substituted linear, branched or cyclic $C_{1-4}$ alkyl or heteroalkyl;
m is independently 2, 3 or 4;

ii) a moiety $L^2$, which is a chemical bond or a spacer, and $L^2$ is bound to a carrier group Z,
wherein $L^1$ is substituted with one to four $L^2$ moieties, optionally, L is further substituted.

Suitable substituents are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

In the present application the following terms are used as described below.

"Prodrug": A prodrug is any compound that undergoes biotransformation before exhibiting its pharmacological effects. Prodrugs can thus be viewed as drugs containing specialized non-toxic protective groups used in a transient manner to alter or to eliminate undesirable properties in the parent molecule.

"Promoiety" refers to the part of the prodrug which is not the biologically active moiety. Promoiety thus refers to the linker and the carrier, if a carrier is present.

"Carrier-linked prodrug" or "carrier prodrug": A carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

"Cascade prodrug": A cascade prodrug is a carrier prodrug for which the cleavage of the carrier group becomes effective only after unmasking an activating group.

"Polymeric cascade prodrug": A polymeric cascade prodrug is a carrier prodrug that contains a temporary linkage of a given active substance with a transient polymeric carrier group for which the cleavage of the carrier becomes effective only after unmasking an activating group.

"Bioprecursor prodrug": A bioprecursor prodrug is a prodrug that does not imply the linkage to a carrier group, but results from a molecular modification of the active principle itself. This modification generates a new compound, able to be transformed metabolically or chemically, the resulting compound being the active principle.

"Biotransformation": Biotransformation is the chemical conversion of substances by living organisms or enzyme preparations.

The previous definitions are based on IUPAC, as given under http://www.chem.qmul.ac.uk/iupac/medchem/ (accessed on 8 Mar. 2004)

"Linker": Cleavage-controlling chemical structures or groups present in carrier prodrugs that are not provided by either the carrier entity or by the drug.

"Sustained release" or "sustained release rate" means that the administration intervals of the respective prodrug are expanded. Drugs with a daily dosage may for example be turned into a sustained release form with a week-long or even longer interval between two administrations.

"Aromatic hydroxyl group containing biologically active moiety D" means the part, e.g. the moiety or fragment, of the prodrug conjugate D-L, which results after cleavage in the drug D-H, the active agent, of known biological activity. "L" in D-L refers to the promoiety. In addition, the subterm "aromatic hydroxyl group containing" means that the respective moiety D and analogously the corresponding drug D-H contain at least one aromatic fragment, and which at least one aromatic fragment is substituted with at least one hydroxyl group. To be aromatic, the number of pi electrons must satisfy the Hükkel rule (4n+2) and cycle has to be planar. Within the scope of the invention, "aromatic hydroxyl group-containing" and "phenolic" are used synonymously.

"Non-biologically active linker" means a linker which does not show pharmacological effects.

Suitable carriers are polymers and can either be directly conjugated to the linker or via a non-cleavable spacer. The term "prodrug according to the invention" refers to carrier-linked prodrugs of biologically active agent, wherein the carrier is PEG or a hydrogel. The terms "PEG prodrug", "PEG-linked prodrug", "hydrogel prodrug" and "hydrogel-linked prodrug" refer to prodrugs of biologically active agents transiently linked to a PEG or to a hydrogel, respectively, and are used synonymously. The term "polymer prodrug" refers to carrier-linked prodrugs of a biologically active agent, wherein the carrier is a polymer.

The term polymer describes a molecule comprised of repeating structural units connected by chemical bonds in a linear, circular, branched, crosslinked or dendrimeric way or a combination thereof, which can be of synthetic or biological origin or a combination of both. Typically, a polymer has a molecular weight of at least 1 kDa.

Polymers are preferably selected from the group consisting of for example, 2-methacryloyl-oxyethyl phosphoyl cholins, hydrogels, PEG based hydrogels, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), polylactic acids), polylactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, mannans, pectins, rhamnogalacturonans, starches, hydroxyalkyl starches, hydroxyethyl starches and other carbohydrate-based polymers, xylans, and copolymers thereof.

More preferably, Z is a biodegradable poly(ethylene glycol) based water-insoluble hydrogel.

The term "poly(ethylene glycol) based" or "PEG based" as understood herein means that the mass proportion of PEG chains in the hydrogel is at least 10% by weight, preferably at least 25%, based on the total weight of the hydrogel. The remainder can be made up of other polymers. Moreover the term "water-insoluble" refers to a swellable three-dimensionally crosslinked molecular network forming the hydrogel. The hydrogel if suspended in a large surplus of water or aqueous buffer of physiological osmolality may take up a substantial amount of water, e.g. up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

The term "PEG" or "PEGylation residue" is used herein exemplary for suitable water-soluble polymers characterized by repeating units. Suitable polymers may be selected from the group consisting of polyalkyloxy polymers, hyaluronic acid and derivatives thereof, polyvinyl alcohols, polyoxazolines, polyanhydrides, poly(ortho esters), polycarbonates, polyurethanes, polyacrylic acids, polyacrylamides, polyacrylates, polymethacrylates, polyorganophosphazenes, polysiloxanes, polyvinylpyrrolidone, polycyanoacrylates, and polyesters. Preferred are polyalkyloxy polymers, especially poly(ethylene glycol) polymers containing at least 10% by weight ethylene oxide units, more preferably at least 25% by weight, even more preferably at least 50% by weight A "hydrogel" may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. The chains of the network are connected in such a fashion that pores exist and that a substantial fraction of these pores are of dimensions between 1 nm and 1000 nm.

"Free form" of a drug refers to the drug in its unmodified, pharmacologically active form, such as after being released from a polymer conjugate.

A strong in vivo/in vitro correlation is observed, if the release kinetics exhibited by a carrier-linked prodrug conjugate according to the invention in vivo has a half-life that is not smaller than half the value exhibited by the same carrier-linked prodrug conjugate in aqueous buffer of pH 7.4 at 37° C. It is understood that in the case of soluble carriers, release kinetics may be recorded as hydrolysis kinetics.

The terms "drug", "biologically active molecule", "biologically active moiety", "biologically active agent", "active agent", and the like mean any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals.

"Spacer" refers to any moiety suitable for connecting two moieties, such as $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl.

"Functional groups" mean groups of atoms within molecules that exhibit a specific chemical activity. Examples are amides, amines, alcohols, carbonyls, carboxylic acids, thiols.

"Protective groups" refers to a moiety which temporarily protects a functional group of a molecule during synthesis to obtain chemoselectivity in subsequent chemical reactions. Protective groups for alcohols are, for example, benzyl and trityl, protective groups for amines are, for example, tert-butyloxycarbonyl, 9-fluorenylmethyloxycarbonyl and benzyl and for thiols examples of protective groups are 2,4,6-trimethoxybenzyl, phenylthiomethyl, acetamidomethyl, p-methoxybenzyloxycarbonyl, tert-butylthio, triphenylmethyl, 3-nitro-2-pyridylthio, 4-methyltrityl.

The term "Protected functional groups" means a functional group protected by a protective group.

"Acylating agent" means a moiety of the structure R—(C=O)—, providing the acyl group in an acylation reaction, optionally connected to a leaving group, such as acid chloride, N-hydroxy succinimide, pentafluorphenol and para-nitrophenol.

"Alkyl" means a straight-chain or branched carbon chain (unsubstituted alkyl). Optionally, each hydrogen of an alkyl carbon may be replaced by a substituent.

"Heteroalkyl" refers to analogs of alkyls in which one or more than one methylene group is replaced by a heteroatom, such as nitrogen, oxygen, sulfur, phosphorus, or boron. If the methylene group is replaced by nitrogen, phosphorous or boron, these heteroatoms may be further substituted. Suitable substituents are alkyl, alkenyl, alkynyl, aryl, heteroalkyl, heteroalkenyl, heteroalkynyl, heteroaryl or halogen moieties (such as those described above). The terms heteroalkenyl and heteroalkynyl are defined accordingly.

"$C_{1-4}$ alkyl" means an alkyl chain having 1 to 4 carbon atoms (unsubstituted $C_{1-4}$ alkyl), e.g. if present at the end of a molecule: methyl, ethyl, n-propyl, isopropyl, n-butyl, isobutyl, sec-butyl tert-butyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Optionally, each hydrogen of a $C_{1-4}$ alkyl carbon may be replaced by a substituent. Accordingly, "$C_{1-50}$ alkyl" means an alkyl chain having 1 to 50 carbon atoms. The term $C_{1-6}$ is defined accordingly.

"$C_{2-50}$ alkenyl" means a branched or unbranched alkenyl chain having 2 to 50 carbon atoms (unsubstituted $C_{2-50}$ alkenyl), e.g. if present at the end of a molecule: —CH=CH$_2$, —CH=CH—CH$_3$, —CH$_2$—CH=CH$_2$, —CH=CH—CH$_2$—CH$_3$, —CH=CH—CH=CH$_2$, or e.g. —CH=CH—, when two moieties of a molecule are linked by the alkenyl group. Optionally, each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur. The term $C_{2-6}$ alkenyl is defined accordingly.

"$C_{2-50}$ alkynyl" means a branched or unbranched alkynyl chain having 2 to 50 carbon atoms (unsubstituted $C_{2-50}$ alkynyl), e.g. if present at the end of a molecule: —C≡CH, —CH$_2$—C≡CH, CH$_2$—CH$_2$—C≡CH, CH$_2$—C≡C—CH$_3$, or e.g. —C≡C— when two moieties of a molecule are linked by the alkynyl group. Optionally, each hydrogen of a $C_{2-50}$ alkynyl carbon may be replaced by a substituent as further specified. Accordingly, the term "alkynyl" relates to a carbon chain with at least one carbon carbon triple bond. Optionally, one or more double bonds may occur. The term $C_{2-6}$ alkynyl is defined accordingly.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated (unsubstituted $C_{3-7}$ cycloalkyl), e.g. cyclopropyl, cyclobutyl, cyclopentyl, cyclohexyl, cyclohexenyl, cycloheptyl. Optionally, each hydrogen of a cycloalkyl carbon may be replaced by a substituent. The term "$C_{3-7}$ cycloalkyl" or "$C_{1-7}$ cycloalkyl ring" also includes bridged bicycles like norbonane (norbonanyl) or norbonene (norbonenyl). Accordingly, "$C_{3-5}$ cycloalkyl" means a cycloalkyl having 3 to 5 carbon atoms.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 4 to 7 membered heterocyclyl).

Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. Optionally, each hydrogen of a 4 to 7 membered heterocyclyl may be replaced by a substituent.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 9 to 11 membered heterobicyclyl).

Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane. Optionally, each hydrogen of a 9 to 11 membered heterobicyclyl may be replaced by a substituent.

In case the prodrugs according to the present invention contain one or more acidic or basic groups, the invention also comprises their corresponding pharmaceutically or toxicologically acceptable salts, in particular their pharmaceutically utilizable salts. Thus, the prodrugs which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Prodrugs which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the prodrugs simultaneously contain acidic and basic groups in the molecule, the invention also includes, in addition to the salt forms mentioned, inner salts or betaines (zwitterions). The respective salts of the prodrugs of the present invention can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency, such as the EMEA (Europe) and/or the FDA (US) and/or any other national regulatory agency for use in animals, preferably in humans.

"Pharmaceutical composition" or "composition" means a composition containing one or more active ingredients, for example a drug or a prodrug, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a prodrug of the present invention and a pharmaceutically acceptable excipient.

"Stable" and "stability" means that within the indicated storage time the polymer conjugates remain conjugated and do not hydrolyze to a substantial extent and exhibit an acceptable impurity profile relating to the biologically active agent. To be considered stable, the composition contains less than 10%, preferably less than 5% of the drug in its free form.

"Therapeutically effective amount" means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician. Within the scope of this invention, therapeutically effective amount relates to dosages that aim to achieve therapeutic effect for an extended period of time, i.e. for 12 hours, or 24 hours, or three days or longer, for instance one week or two weeks.

"Excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions.

"Dry composition" means that the prodrug composition is provided in a dry form in a container. Suitable methods for drying are spray-drying and lyophilization (freeze-drying). Such dry composition of prodrug has a residual water content of a maximum of 10%, preferably less than 5% and more preferably less than 2% (determined according to Karl Fischer). The preferred method of drying is lyophilization.

"Lyophilized composition" means that the prodrug composition was first frozen and subsequently subjected to water reduction by means of reduced pressure. This terminology does not exclude additional drying steps which occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

"Reconstitution" means the addition of a liquid to bring back the original form of a composition.

"Reconstitution solution" refers to the liquid used to reconstitute the dry composition of a prodrug prior to administration to a patient in need thereof.

"Container" means any container in which the prodrug composition is comprised and can be stored until reconstitution.

"Buffer" or "buffering agent" refers to chemical compounds that maintain the pH in a desired range. Physiologically tolerated buffers are, for example, sodium phosphate, succinate, histidine, bicarbonate, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

A "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as monosodium glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; poly(ethylene glycol); pluronics; hydroxyalkyl starches, e.g. hydroxyethyl starch (HES), and combinations thereof.

"Surfactant" refers to wetting agents that lower the surface tension of a liquid.

"Isotonicity modifiers" refer to compounds which minimize pain that can result from cell damage due to osmotic pressure differences at the injection depot.

The term "stabilizers" refers to compounds used to stabilize the polymer prodrug. Stabilisation is achieved by strengthening of the protein-stabilising forces, by destabilisation of the denatured state, or by direct binding of excipients to the protein.

"Anti-adsorption agents" refers to mainly ionic or nonionic surfactants or other proteins or soluble polymers used to coat or adsorb competitively to the inner surface of the composition's container. Chosen concentration and type of excipient depends on the effect to be avoided but typically a monolayer of surfactant is formed at the interface just above the CMC value.

"Oxidation protection agents" refers to antioxidants such as ascorbic acid, ectoine, glutathione, methionine, monothioglycerol, morin, polyethylenimine (PEI), propyl gallate, vitamin E, chelating agents such aus citric acid, EDTA, hexaphosphate, thioglycolic acid.

"Antimicrobial" refers to a chemical substance that kills or inhibits the growth of microorganisms, such as bacteria, fungi, yeasts, protozoans and/or destroys viruses.

"PEG based" as understood herein means that the mass proportion of PEG chains in the hydrogel is at least 10% by weight, preferably at least 25%, based on the total weight of the hydrogel. The remainder can be made up of other spacers and/or oligomers or polymers, such as oligo- or polylysines.

The term "hydrolytically degradable" or "biodegradable" refers within the context of the present invention to linkages which are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates. It is understood that for in vitro studies accelerated conditions like, for example, pH 9, 37° C., aqueous buffer, may be used for practical purposes.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The present invention addresses disadvantages of previous carbamate prodrugs, such as, for example, safety issues of hydrolysis products and therapeutically unsuitable hydrolysis rates. As there is a need for advanced carrier-linked prodrugs of drugs containing aromatic hydroxyl groups, it was now surprisingly found that drugs containing aromatic hydroxyl groups can be conjugated to polymeric carriers via secondary carbamate-containing linkers and that such carrier-linked prodrugs achieve drug releases with therapeutically useful half-lives.

Such polymeric secondary carbamate prodrugs allow for an extended, controlled release mechanism, which reduces the frequency with which a drug has to be taken. Furthermore, as isocyanate formation is not observed for secondary carbamate hydrolysis, such groups offer more predictable release rates and predictable hydrolysis products with a greatly improved safety profile compared to primary carbamates.

The invention provides for carrier-linked carbamate prodrugs which are characterized by a carrier connected to a linker, wherein the linker has a first and a second amine group and is connected to the drug moiety through a carbamate bond connecting the second amine group and the drug moiety's aromatic hydroxyl group. Such carbamate prodrugs are further characterized by the linker's second amine group being a secondary amine group. The carrier is connected to the amine-containing linker via a permanent linkage, and the carbamate bond between the promoiety and the drug moiety is a temporary linkage exhibiting extended autohydrolysis at a therapeutically useful rate at pH 7.4 and 37° C.

Due to the presence of a permanent bond between the carrier and the carbamate linker, the prodrugs according to the present invention ensure release of unmodified native drug molecules from a stable conjugate comprising carrier and linker moiety. Furthermore, in these linker structures, the presence of the carrier entity still allows for therapeutically useful autohydrolysis rates, an essential prerequisite for prodrug applications.

In this invention, the hydrolytic lability required for a temporary linkage is introduced into the prodrug carbamate bond by selecting the structural properties of the linker for neighboring group participation. In carbamate bond cleavage under physiological conditions, the cleavage products are a free aromatic hydroxyl group containing moiety, hydrogencarbonate and an amine-containing residue. For a given phenolic moiety, a corresponding aliphatic promoiety linked through a carbamate is highly likely to exhibit significant hydrolytic stability and is therefore unlikely to release the phenolic drug moiety in a therapeutically useful time frame. For this reason, neighboring group participation is desirable to introduce enzyme-independent lability into the carbamate bond. Such neighboring group may be a first amine group. If the linker structure is designed such that the first amine may intramolecularly catalyze the hydrolysis of the carbamate bond to the drug moiety, the hydrolysis of the carbamate bond may be facilitated to the extent that hydrolysis under physiological conditions in a time range useful for drug delivery is possible. Such preferred first amine groups may be primary, secondary or tertiary amine or quaternary ammonium cations.

Corresponding prodrugs are composed of an aliphatic linker containing a first amine, a permanent linkage to a polymer carrier, wherein the linker is conjugated to an aromatic hydroxyl group-containing drug by means of a temporary carbamate bond involving a second amine provided by the aliphatic linker, and wherein the second amine forming the carbamate bond is a secondary amine.

Preferably, linkers of the present invention have a hydrolysis rate between 1 h and 2 years at pH 7.4 and 37° C. and hydrolysis rates in buffer and plasma are essentially identical, i.e. the hydrolysis rates exhibit a strong in vivo/in vitro correlation.

Preferably, D-His a small molecule bioactive agent or a biopolymer.

Preferably, D-His a biopolymer selected from the group of biopolymers consisting of proteins, or polypeptides.

Preferably, D-His a polypeptide containing a phenolic moiety selected from the group of polypeptides consisting of ACTH, adenosine deaminase, agalsidase, alfa-1 antitrypsin (AAT), alfa-1 proteinase inhibitor (API), alteplase, amylins (amylin, symlin), anistreplase, ancrod serine protease, antibodies (monoclonal or polyclonal, and fragments or fusions), antithrombin III, antitrypsins, aprotinin, asparaginases, atosiban, biphalin, bivalirudin, bone-morphogenic proteins, bovine pancreatic trypsin inhibitor (BPTI), cadherin fragments, calcitonin (salmon), collagenase, complement C1 esterase inhibitor, conotoxins, cytokine receptor fragments, DNase, dynorphine A, endorphins, enfuvirtide, enkephalins, erythropoietins, exendins, factor VII, factor VIIa, factor VIII, factor VIIIa, factor IX, fibrinolysin, fibroblast growth factor (FGF), growth hormone releasing peptide 2 (GHRP2), fusion proteins, follicle-stimulating hormones, gramicidin, ghrelin, desacyl-ghrelin, granulocyte colony stimulating factor (G-CSF), galactosidase, glucagon, glucagon-like peptides, glucocerebrosidase, granulocyte macrophage colony stimulating factor (GM-CSF), human heat shock proteins (HSP), phospholipase-activating protein (PLAP), gonadotropin chorionic (hCG), hemoglobins, hepatitis B vaccines, hirudin, human serine protease inhibitor, hyaluronidases, idurnonidase, immune globulins, influenza vaccines, interleukins (1 alfa, 1 beta, 2, 3, 4, 6, 10, 11, 12, 13, 21), IL-1 receptor antagonist (rhIL-1ra), insulins, insulin like growth factors, insulin-like growth factor binding protein (rhIGFBP), interferons (alfa 2a, alfa 2b, alfa 2c, beta 1a, beta 1b, gamma 1a, gamma 1b), intracellular adhesion molecule, keratinocyte growth factor (KGF), P-selectin glycoprotein ligand (PSGL), transforming growth factors, lactase, leptin, leuprolide, levothyroxine, luteinizing hormone, lyme vaccine, natriuretic peptides (ANP, BNP, CNP and fragments), neuropeptide Y, pancrelipase, pancreatic polypeptide, papain, parathyroid hormone, PDGF, pepsin, peptide YY, platelet activating factor acetylhydrolase (PAF-AH), prolactin, protein C, thymalfasin, octreotide, secretin, sermorelin, soluble tumor necrosis factor receptor (TNFR), superoxide dismutase (SOD), somatropins (growth hormone), somatoprim, somatostatin, streptokinase, sucrase, terlipressin, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urodilatin, urate oxidase, urokinase, vaccines, vascular endothelial growth factor (VEGF), vasoactive intestinal peptide, vasopressin, ziconotide, lectin and ricin.

Preferably, D-H is a protein prepared by recombinant DNA technologies.

Preferably, D-H is a protein selected from the group of proteins consisting of antibodies, antibody fragments, single chain antigen binding proteins, catalytic antibodies and fusion proteins.

More preferably, D-H is a protein selected from the group of proteins consisting of antibody fragments, single chain antigen binding proteins, catalytic antibodies and fusion proteins.

Preferably, D-H is a small molecule bioactive agent selected from the group of agents consisting of central nervous system-active agents, anti-infective, anti-allergic, immunomodulating, anti-obesity, anticoagulants, antidiabetic, anti-neoplastic, antibacterial, anti-fungal, analgesic, contraceptive, anti-inflammatory, steroidal, vasodilating, vasoconstricting, and cardiovascular agents with at least one aromatic hydroxyl group.

D may be any aromatic hydroxyl-containing biologically active moiety known to a person skilled in the art, which is derived from the corresponding biologically active drug D-H obtained after cleavage of D from the drug linker conjugate D-L. As indicated above, D contains at least one aromatic fragment, which at least one aromatic fragment is substituted with at least one hydroxyl group and said hydroxyl group is in turn connected to the amine-containing moiety $L^1$ by forming a carbamate bond.

To be aromatic, the number of pi electrons must satisfy the Hückel rule (4n+2) and the cycle has to be planar. D may contain further substituents besides at least one aromatic hydroxyl group, such as further aliphatic or aromatic hydroxyl groups, amines, amides, carbonyls, carboxylic acids, thiols or halogens. The term "aromatic" or "aromatic fragment" means any aromatic fragment known to a person skilled in the art such as aryl, e.g. phenyl or naphthyl, or heteroaryl, such as aromatic 4 to 7 membered heterocyclyls or aromatic 9 to 11 membered heterobicyclyls. Such aromatic heterocyclyls are, for example, furans, thiophenes, pyrroles, imidazoles, pyrazoles, oxazoles, isoxazoles, thiazoles, isothiazoles, thiadiazoles, thiadiazolines, pyridines, pyridazines, pyrazines, pyrimidines, tetrazoles and thriazoles.

The aromatic fragment comprises mono-, bi- or polycyclic fragments. In case of bi- or polycyclic fragments it is sufficient that only one of said cycles is aromatic. D may contain two or more further aromatic fragments as defined before, which are bound to the first aromatic fragment, which is substituted with at least one amino group, either directly by a chemical bound or by a spacer. Said two or more additional aromatic fragments may also contain at least one amino group. In the following, D is defined by the corresponding aromatic hydroxyl containing biologically active drug D-H.

In one embodiment, D-H may be selected from the group of aromatic hydroxyl containing biologically active agents consisting of (−)-Chicoric acid, (−)-cis-Resorcylide, (−)-Conophylline, (−)-Epigallocatechin gallate, (−)-Gossypol, (−)-Indocarbazostatin B, (−)-Salbutamol hydrochloride, (−)-Salmeterol, (−)-Subersic acid, (−)-Vexibinol, (+)-alpha-Viniferin, (+)-Etorphine, (+)-Indocarbazostatin, (+)—SCH-351448, (R)-Albuterol hydrochloride, (R)-Gossypol, (R)-Tulobuterol, (R,R)-Formoterol tartrate, (S)-(+)-Curcuphenol, (S)-Methylnaltrexone bromide, [111In-DTPA-Pro1,Tyr4]bombesin, [8]-Gingerol, [99Tc]Demobesin 3, [99Tc]Demobesin 4, [Arg(Me)9] MS-10, [D11G,K26R,Y40YR]-Plectasin, [D11G,M13K,K26R,Y40YR]-Plectasin, [D9N,M13L,Q14R]-Plectasin, [D9S,Q14K,V36L]-Plectasin, [D-Tyr1,Arg(Me)9] MS-10, [D-Tyr1,AzaGly7,Arg(Me)9] MS-10, [D-Tyr1] MS-10, [Gln30]-Pancreatic polypeptide(2-36), [Glu10,Nle17,Nle30]-Pancreatic polypeptide (2-36), [Glu10]-Pancreatic polypeptide(2-36), [Leu13]-Motilin, [N5R,M13Y,N17R]-Plectasin, [Nie17,Nle30]-Pancreatic polypeptide(2-36), [psi [CH2NH]Tpg4]Vancomycin aglycon, [Trp19] MS-10, 13-Deoxyadriamycin hydrochloride, 13-Deoxydoxorubicin hydrochloride, 14-Methoxymetopon, 14-Phenylpropoxymetopon, 17beta-Estradiol, 18,19-Dehydrobuprenorphine hydrochloride, 2,12-Dimethyleurotinone, 2'-Hydroxymatteucinol, 2-Methoxyestradiol, 2-Methyleurotinone, 3,5-Dicaffeoylquinic acid, 3-Bromodiosmetine, 3-Bromodiosmine, 3-Chlorodiosmetine, 3-Chlorodiosmine, 3-O-Methylquercetin, 4',7,8-Trihydroxyisoflavone, 4-Aminosalicylic acid, 4'-Dehydrodeacetylgriseusin A, 4-Demethylpenclomedine, 4'-epi-Adriamycin, 4'-epi-Doxorubicin, 4-Hydroxyatomoxetine, 4-Iodopropofol, 5-Aminosalicylic acid, 5-Iodofredericamycin A, 5-O-(E)-p-Coumaroylquinic acid, 5Z-7-Oxozeaenol, 6-Carboxygenistein, 6-O-mPEG4-Nalbupine, 6-O-mPEG5-Nalbuphine, 7-Chlorokynurenic acid, 7-Methylcapillarisin, 7-Monohydroxyethylrutoside, 8(R)-Fluoroidarubicin hydrochloride, 8',9'-Dehydroascochlorin, 8-Carboxy-iso-iantheran A, 8-Paradol, 8-Prenylapigenin, 8-Prenylnaringenin, 9-Hydroxycrisamicin A, A-42867 pseudoaglycone, Abarelix, Acacetin, Acetaminophen, Aclacinomycin A, Aclacinomycin-X, Aclarubicin, Acolbifene hydrochloride, Acotiamide hydrochloride hydrate, Acrovestone, Actinoplanone A, Actinoplanone B, Aculeacin Agamma, Adaphostin, Adarotene, Adxanthromycin A, Aerothricin 1, Aerothricin 16, Aerothricin 41, Aerothricin 45, Aerothricin 50, Aerothricin 55, Afamelanotide, Ajulemic acid, Albolabrin, Albuterol nitrate, Albuterol sulfate, Alchemix, Aldifen, alpha-Human atrial natriuretic polypeptide, alpha-Mangostin, alpha-Methylepinephrine, alpha-Methylnorepinephrine, alpha-Peltatin ((−)-enantiomer), Altromycin A, Altromycin B, Altromycin C, Altromycin D, Altromycins, Alvimopan hydrate, Alvocidib hydrochloride, Amamistatin A, Amamistatin B, Amarogentin, Amelubant, Amidox, Aminocandin, Amodiaquine, Amoxicillin, Amoxicillin trihydrate, Amoxycillin trihydrate, Amrubicin hydrochloride, Amurensin H, Angiopeptin acetate, Angiotensin II (human), Anguillosporal, Anidulafungin, Ankinomycin, Annamycin, Annulin C, Annamycin, Antimycin A11, Antimycin A12, Antimycin A13, Antimycin A14, Antimycin A15, Antimycin A16, Apalcillin sodium, Apcitide technetium (99 mTc), Apicularen A, Apicularen B, Apigenin, Apomine, Apomorphine hydrochloride, Arbidol, Arbutamine hydrochloride, Arenicin, Arenicin-1, Arenicin-2, Arformoterol tartrate, Argiopine, Argiotoxin-636, Artepillin C, Arzoxifene hydrochloride, Aspoxicillin, Astringinine, Atalaphillidine, Atalaphillinine, Atraric acid, Atrial natriuretic factor (99-126), Avorelin, Axitirome, Azaresveratrol, Anatoxin, Azelastine embonate, Azepinostatin, Azodisal disodium, Baicalein, Baicalin, Balanol, Balhimycin, Balsalazide disodium, Banoxantrone, Bazedoxifene acetate, Bazedoxifene hydrochloride, Bedoradrine sulfate, Benadrostin, Benanomicin A, Benanomicin B, Benastatin A, Benastatin B, Benastatin C, Benastatin D, Benzalazine, Benzbromaron, Benzbromarone, Berefrine, Berupipam maleate, beta-Guttiferin, beta-Mangostin, Biemnidin, Biochanin A, Bioxalomycin alpha 1, Bioxalomycin alpha2, Bismuth subsalicylate, Bisphenol, Bivalirudin, Bix, Bizelesin, Bogorol A, Brandisianin A, Brandisianin B, Brandisianin C, Brasilicardin A, Brevifolin carboxylic acid, Breynin A, Breynin B, Bromotopsentin, Buflomedil pyridoxalphosphate, Buprenorphine hydrochloride, Burefrine, Buserelin acetate, Butein, Buteranol, Butorphan, Butorphanol tartrate, Calebin A, Calocoumarin A, Caloporoside D, Caloporoside E, Caloporoside F, Calphostin A, Calphostin B, Calphostin C, Calphostin D, Calphostin I, Capillarisin, Capsazepine, Carbazomadurin A, Carbazomadurin B, Carbetocin, Carbidopa, Carmoterol hydrochloride, Carperitide, Caspofungin acetate, Cassigalol A, Catechaldehyde, Cavtratin, Cefetecol, Cefoperazone sodium, Cefpiramide sodium, Cefprozil, Cefprozil monohydrate, Cetrorelix acetate, Chaetoatrosin A, Chafuroside, Chicoric acid-(−), Chloroorienticin A, Chloroorienticin B, Chloropeptin II, Chondramide A, Chondramide B, Chondramide C, Chondramide D, Cicletanine, Cinnatriacetin A, Cinnatriacetin B, cis-6-Shogaol, Citpressine I, Citreamicin-alpha, Citreamicin-eta, Citrusinine-I, Clausenamine A, Clioquinol, Clostomycin B1, Combretastatin A-1, Combretastatin A-2, Combretastatin A-3, Combretastatin B-1, Combretastatin B-2, Combretastatin B-3, Combretastatin B-4, Combretastatin D-1, Combretastatin D-2, Complestatin, Conantokin-R, coniferol alcohol, Conophylline, Contulakin G, Coproverdine, Corylifolinin, Corynecandin, Cosalane, Crisamicin C, Crobenetine, Crobenetine hydrochloride, Cucoline, Curtisian A, Curtisian B, Curtisian D, Cyanidin, Cyanidin chloride monohydrate, Cyanidol chloride, Cyclocommunol, Cyclopropadicicol, Cyclotheonamide A, Cyclothialidine, Cycloviolin A, Cycloviolin B, Cycloviolin C, Cycloviolin D, Cyrtominetin, Cytogenin, Cytosporone B, Cytotrienin A, Cytotrienin I, Cytotrienin II, Dactylocycline A, Dactylocycline B, DADMe-Immucillin-G, DADMe-Immucillin-H, Dalargin, Dalbavancin, D-allo-Ileu3 PYY(3-36), Damnacanthal, Damuncantal, Daphnodorin A, Daphnodorin B, Daphnodorin C ((−)-enantiomer), Darbufelone, Darbufelone mesilate, Daunomycin, Daunorubicin, Daurichromenic acid, Davidigenin, Deacetyl moxisylyte hydrochloride, Decaplanin, Decyl gallate, Deferasirox, Dehydroequol, Dehydrozingerone, Dekafin 10, Delphinidin, Delphinidin chloride, Delphinidol, DELTA9-Tetrahydrocannabinol, Deltorphin E, Denopamine, Deoxymulundocandin, Dersalazine, Desacetylravidomycin N-Oxide, Desglugastrin tromethamine, Deslorelin, Desmopressin acetate, Desulfated hirudin (54-65), Desulfated hirugen, Desvenlafaxine succinate, Dexanabinol, Dexanabinone, Dextronatrin, Dextrorphan, Dexylosylbenanomycin A, D-Fluviabactin, Diazaphilonic acid, Diazepinomicin, Didehydro-epsilon-viniferin, Dieckol, Difimicin, Diflunisal, Dihydrexidine, Dihydroavenanthramide D, Dihydrogranaticin B, Dihydrohonokiol B, Dihydroraloxifene, Dilevalol, Dilevalol hydrochloride, Dinapsoline, Dinofan, Dinoxyline, Dipotassium gossypolate, Disagregin, Disoprofol, Dobutamine hydrochloride, Dobutamine phosphate, Dopexamine, Dopexamine hydrochloride, Dosmalfate, Doxorubicin hydrochloride, Doxorubicin, morpholinyl, DoxoTam 12, Doxycycline hyclate, Doxycycline hydrochloride ethanol hydrate, Dronabinol, Droxidopa, Dumorelin, Duocarmycin B1, Duocarmycin B2, Duocarmycin C1, Duocarmycin C2, Dutomycin, Dynemicin A, Dynemicin C, Dyofin-1, Dyofin-2, Dyofin-9, Echistatin, Econazole sulfosalicylate, Ecopipam, Ecteinascidin 1560, Ecteinascidin 722, Ecteinascidin 729, Ecteinascidin 736, Ecteinascidin 743, Ecteinascidin 745, Ecteinascidin 757, Ecteinascidin 770, Ecteinascidin 875, Edotecarin, Edotreotide yttrium, Efepristin, Eflucimibe, Eflumast, Eformoterol fumarate, Eldacimibe, Ellagic acid-4-gallate, Elliptinium acetate, Elsibucol, Eltrombopag olamine, Emodin, Emodol, Emoxyl, Enazadrem, Endothelin, Endothelin 1, Enfuvirtide, Enofelast, Entacapone, Enteric-Coated Mycophenolate Sodium, ent-Estriol, ent-Etorphine, Ephdine, Epidoxoform, Epidoxorubicin, Epigallocatechin gallate, Epigallocatechin-3-gallate, Epirubicin hydrochloride, Eplivanserin, Eplivanserin fumarate, Eplivanserin mesilate, Epocarbazolin A, Epocarbazolin B, Eprotirome, Eptazocine hydrobromide, Erabulenol A, Erabulenol B, Eremomycin, Erythromycin salnacedin, Eserine salicylate, Estetrol, Estradiol, Estriol, Etalocib sodium, Etamsylate, Ethamsylate, Ethinyl estradiol, Ethinylestradiol, Ethinyloestradiol, Ethyl gallate, Etoposide, Eurocin, Eurotinone, Euxanthone, Evernimicin, Exifone, Ezetimibe, Factor P-Zyma, Fadolmidine hydrochloride, Favipiravir, Feglymycin, Feglymycine, Fenoldopam mesilate, Fenoterol hydrobromide, Ferpifosate sodium, Fidaxomicin, Fidexaban, Flavalfate, Flavopiridol, Fluostatin A, Fluostatin B, Foetidine 1, Foetidine 2, Folipastatin, Formobactin, Formoterol fumarate, Fosopamine, Frederine, Frog neuromedin U, Fulvestrant, Furaquinocin A, Furaquinocin B, Fusacandin A, Fusacandin B, Fusidienol, Gaboxadol, Galactomycin I, Galactomycin II, Galarubicin hydrochloride, Gallinacin 1, Gallinacin 1alpha, Galparan, Gambogic acid, gamma-Mangostin, gamma-Tocotrienol, Ganirelix, Ganirelix acetate, Garvalone C, Garveatin E, Garveatin F, Genistein-7-phosphate, Gibbosin, Gigantol, Gilvusmycin, Gimeracil, Gimestat, Glucagon-like peptide I (7-37), Glucopiericidinol A1, Glucopiericidinol A2, Gludopa, Glycothiohexide alpha, Goserelin, Granaticin B, Griseusin C, Hatomarubigin A, Hatomarubigin B, Hatomarubigin C, Hatomarubigin D, Heliquinomycin, Helvecardin A, Helvecardin B, Hericenal A, Hericenal B, Hericenal C, Herpefungin, Hidrosmin, Hidrosmina, Hirudin desulfated, Hirulog-1, Histrelin, Histrelin acetate, Hongoquercin A, Hongoquercin B, Honokiol diepoxide, Honokiol diepoxide, Human adrenomedullin, Human adrenomedullin (22-52), Human angiotensin II, Hydromorphone methiodide, Hydroxyakalone, Hymenistatin 1, Hypeptin, Hypericin, Hyperin, Hyperoside, Icariin, Idarubicin hydrochloride, Idronoxil, Ifenprodil, Imidacrine, Imidazoacridinone, Incyclinide, Indacaterol, Indanocine, Insulin chain B (9-23) peptide, Integracin A, Integracin B, Integracin C, Integramycin, Integrastatin A, Integrastatin B, Intoplicine, Iodochlorhydroxyquin, Iododiflunisal, Iodorubidazone (p), Iolopride (1231), Ioxipride, Iralukast, Iralukast sodium, Irciniastatin A, Irciniastatin B, Isalmadol, Iseganan hydrochloride, Isobavachalcone, Isochlorogenic acid a, Isodoxorubicin, Isoiantheran A, Isoliquiritigenin, Isomolpan hydrochloride, Isoquine, Isovanihuperzine A, Jadomycin B, Jaspamide, Jasplakinolide, Kadsuphilin C, Kaitocephalin, Kampanol A, Kampanol B, Kanglemycin A, Kapurimycin A1, Kapurimycin A2, Kapurimycin A3, Karnamicin B1, Kassinatuerin-1, Kehokorin D, Kehokorin E, Keoxifene hydrochloride, Kigamicin A, Kigamicin B, Kigamicin C, Kigamicin D, Kigamicin E, Kigamicinone, Kistamicin A, Klainetin A, Klainetin B, Kodaistatin A, Kodaistatin B, Kodaistatin C, Kodaistatin D, Korupensamine A, Korupensamine B, Korupensamine C, Korupensamine D, Kosinostatin, Kukoline, Kushenol F, Kushnol F, Labetalol hydrochloride, Laccaridione A, Lactonamycin, Lactosylphenyl trolox, Ladirubicin, Lamellarin alpha 20-sulfate sodium salt, Lamifiban, Lanreotide acetate, Lasofoxifene, Lasofoxifene tartrate, Latamoxef sodium, L-Chicoric acid, L-DOPA 3-O-glucoside, L-DOPA 4-O-glucoside, L-Dopa methyl ester hydrochloride, L-Dopamide, Lecirelin, Leconotide, Ledazerol, Leuprolide acetate, Leuprorelin acetate, Leurubicin, Levalbuterol hydrochloride, Levodopa, Levodopa 3-O-glucoside, Levodopa 4-O-glucoside, Levodopa methyl ester hydrochloride, Levorphanol tartrate, Levosalbutamol hydrochloride, L-Fluviabactin, L-Fluvibactin, L-Fluvibactine, Linderol A, Linopristin, Linopristine, Lipiarmycin, Lipiarmycin A3, Lipiarmycin B3, Lipiarmycin B4, Liquiritin apioside, Liraglutide, Lithospermic acid B magnesium salt, Lobatamide C, Lobatamide F, Loloatin B, Luminacin D, Luteolin, Macrocarpin A, Macrocarpin B, Magnesium lithospermate B, Magnesium salvianolate B, Magnesium tanshinoate B, Makaluvamine D, Makaluvamine E, Makaluvamine F, Malonoben, Maltolyl p-coumarate, Mannopeptimycin beta, Manzamine F, Marmelin, Masoprocol, MASTPROM, Matteuorienate A, Matteuorienate B, Matteuorienate C, Medicarpin, Melanotan, Melanotan I, Melevodopa hydrochloride, Mellein, Meluadrine, Meluadrine tartrate, Memno-peptide A, Meptazinol hydrochloride, Mesalamine, Mesalazine, Metaproterenol sulfate, Metaraminol, Meterelin, Methanobactin, Methyl gallate, Methyldopa, Methylnaltrexone bromide, Metirosine, Metyrosine, Micafungin sodium, Michellamine B, Miconazole sulfosalicylate, Microcin 25, Microcin J25, Mideplanin, Mimopezil, Minocycline hydrochloride, Miproxifene, Mitoxantrone hydrochloride, Mitoxantrone hydrochloride, Mivazerol, Modecamide, Mollugin, Morphine 6-O-glucuronide, Morphine glucuronide, Morphine hydrochloride, Morphine sulfate, Morphine sulphate, Moxalactam disodium, Moxifetin hydrogen maleate, Multiple sclerosis vaccine, Mumbaistatin, muO-Conotoxin MrVIB, Mureidomycin A, Mureidomycin B, Mureidomycin C, Mureidomycin D, Mureidomycin E, Mureidomycin F, Mureidomycins, Mycophenolate mofetil, Mycophenolate sodium, Mycophenolic acid sodium salt, Myrciacitrin I, Myrciacitrin II, Myrciaphenone B, Myriceric acid A, Mytolbilin, Mytolbilin acid, Mytolbilin acid methyl ester, Mytolbilinol, Naamidine A, Nabilone, N-Acetylcolchinol, Nafarelin acetate, Nagrestipen, Nalbuphine hydrochloride, Nalfurafine hydrochloride, N-Allylsecoboldine, Nalmefene, Nalmetrene, Naloxone hydrochloride, Naltrexone hydrochloride, Naltrindole, Napsamycin A, Napsamycin B, Napsamycin C, Napsamycin D, Nardeterol, NCP-tazop sine, N-Cyclopentyl-tazop sine, Nebicapone, Nelfinavir mesilate, Nemorubicin, Neparensinol A, Neparensinol B, Neparensinol C, Nerfilin I, Neuromedin U-25, Neutrophil-activating factor, Nicanartine, Nitecapone, Nitrofen, Nitrophene, N-Methylhydromorphonium iodide, Nocardione A, Nocathiacin I, Nocathiacin II, Nocathiacin III, Nocathiacin IV, NO-Mesalamine, Nordamnacanthal, Nordamunacantal, Nordihydroguaiaretic acid, Norkurarinone, Nostocyclopeptide M1, Nothramicin, N-tert butyl isoquine, Obelmycin H, Ochracin, Ochromycinone, Octreother, Octyl gallate, Odapipam acetate, O-Demethylchlorothricin, O-Demethylmurrayafoline A, O-Desmethylvenlafaxine succinate, Oenothein B, Okicenone, Olanzapine pamoate, Olcegepant, Olsalazine sodium, omega-Conotoxin CVID, omega-Conotoxin MVIIA, Onjixanthone I, Onjixanthone II, Oolonghomobisflavan A, Oolonghomobisflavan C, Orciprenaline sulphate, Orienticin A, Orienticin B, Orienticin C, Orienticin D, Oritavancin, Orniplabin, Orthosomycin A, Orthosomycin B, Orthosomycin C, Orthosomycin D, Orthosomycin E, Orthosomycin F, Orthosomycin G, Orthosomycin H, Osutidine, OTAC, Oximidine III, Oxymetazoline hydrochloride, Oxymorphazole dihydrochloride, Oxymorphone hydrochloride, Oxyphenarsine, Oystrisin, Ozarelix, Paeciloquinone A, Paeciloquinone B, Paeciloquinone D, Pancratistatin-3,4-cyclic phosphate sodium salt, Pannorin, Papuamide A, Papuamide B, Papuamide C, Papuamide D, Paracetamol, Paradol-8, Parvisporin B, PEG-vancomycin, Penicillide, Pentafuside, Pentazocine hydrochloride, Pepticinnamin E, Peptide Leucine Arginine, Phaffiaol, Phakellistatin 7, Phakellistatin 8, Phakellistatin 9, Phenochalasin A, Phenoxodiol, Phentolamine mesilate, Phlorofucofuroeckol, Phlorofucofuroeckol A, Phomopsichalasin, Phthalascidin, Physostigmine salicylate, Piceasin, Piceatannol, Pidobenzone, Pidorubicin, Pinocembrin, Pipendoxifene, Pirarubicin, Pirbuterol hydrochloride, Pirenoxine, Pirfenoxone, Pittsburgh Compound B, Plantagoside, Platencin, Platensimycin, Pluraflavin A, Pluraflavin B, Pluraflavin E, Pneumocandin A0, Pneumocandin B0, Pneumocandin B0 2-phosphate, Pneumocandin D0, Polyestradiol phosphate, Polyketomycin, Popolohuanone E, Pradimicin A, Pradimicin B, Pradimicin C, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Pramlintide acetate, Prinaberel, Prisotinol, Pristinamycin IA, Pristinamycin IB, Probucol, Procaterol hydrochloride hemihydrate, Propeptin, Propeptin T, Propofol, Propyl gallate, Protegrin IB-367, Protocatechuic acid, Protocatechuic aldehyde, Pseudohypericin, Psymberin, Purpuromycin, Pyridavone, Pyrindamycin A, Pyrindamycin B, Pyrphenoxone, Quercetin 3-galactoside, Quercetin 3-O-beta-D-galactopyranoside, Quercetin-3-O-methyl ether, Quinagolide hydrochloride, Quinobene, Quinupristin mesilate, rac-Apogossypolone, rac-Tolterodine, Radolmidine hydrochloride, Raloxifene hydrochloride, Ramoplanin A'1, Ramoplanin A'2, Ramoplanin A'3, Ramorelix, Rancinamycin IV, Rat adrenomedullin, Ravidomycin N-Oxide, Rawsonol, Reblastatin, Recombinant Jerdostatin, Relaxin-3/INSL5 chimeric peptide, Reproterol hydrochloride, Resobene, Resorthiomycin, Resveratrol, Retaspimycin hydrochloride, Rhodiocyanoside B, Rhododaurichromanic acid A, Rhododaurichromenic acid, Rifabutin, Rifalazil, Rifamexil, Rifampicin, Rifampin, Rifapentine, Rifaximin, Rimoterol hydrobromide, Riodoxol, r-Jerdostatin, Rohitukine, Rotigaptide, Rotigotine, Roxindole mesilate, Ruboxyl, Rufigallol, Rumycin 1, Rumycin 2, Russuphelin A, Sabarubicin hydrochloride, Saintopin, Saintopin E, Sakyomicin A, Sakyomicin E, Salazodine, Salazopyridazin, Salazosulfapyridine, Salbutamol nitrate, Salbutamol sulfate, Salcaprozic acid sodium salt, Salicylazobenzoic acid, Salicylihalamide A, Salicylihalamide B, Saliphenylhalamide, Salmaterol, Salmeterol, Salmeterol xinafoate, Saloxin, Salvianolic acid L, Sampatrilat, Sanglifehrin A, Sanglifehrin B, Sanglifehrin C, Sanglifehrin D, Saptomycin D, Sapurimycin, Saricandin, Secoisolariciresinol diglucoside, Seglitide, Semorphone hydrochloride, Sermorelin, Shiga vaccine, Shishijimicin A, Shishijimicin B, Shishijimicin C, Siamycin I, Siamycin II, Sibenadet hydrochloride, Sifuvirtide, Silychristin, Sinomenine, Sivifene, Siwenmycin, Sodium azodisalicylate, Sootepenseone, Sophoraflavanone G, Spinorphin, Spinosulfate A, Spinosulfate B, Spiroximicin, Stachybocin A, Stachybocin B, Stachybocin C, Stachybotrin C, Stachybotrydial, Staplabin, Stearyl-norleucine-VIP, Sterenin A, Sterenin C, Sterenin D, Streptopyrrole, Succinobucol, Sulfasalazine, Sulphasalazine, Sulphazocine, Super-Leu-Dox, Susalimod, Symbioimine, Synthetic neutrophil inhibitor peptide, Syriacusin A, Syriacusin B, Syriacusin C, Tageflar, Taiwanhomoflavone A, Talnetant, TAP-doxorubicin, Tapentadol hydrochloride, Taramanon A, Tazofelone, Tazopsine, Tebufelone, Technetium (99 mTc) apcitide, Technetium (99 mTc) depreotide, Technetium Tc 99m depreotide, Teicoplanin-A2-1, Teicoplanin-A2-2, Teicoplanin-A2-3, Teicoplanin-A2-3, Teicoplanin-A2-5, Telavancin hydrochloride, Temoporfin, Teniposide, Tenuifoliside A, Tenuifoliside B, Tenuifoliside C, Terbutaline sulfate, Terlipres sin, Terprenin, Tetracycline hydrochloride, Tetragalloylquinic acid, Tetrahydrocurcumin, Tetrahydroechinocandin B, Tetrahydroswertianolin, Textilinin-1, Thanatin, Thenorphine, Theophylline rutoside, Theprubicin, Thiazinotrienomycin B, Thiazinotrienomycin F, Thiazinotrienomycin G, Thielavin G, Thielocin B3, Thienorphine, Thiocoraline, Thiocoraline A, Thiocoraline NF, Thr10-Contulakin G, Thymopentin, Tiacumicin B, Tifuvirtide, Tigecycline, Tigilcycline, Tipelukast, Tocotrienol, Tokaramide A, Tolcapone, Tolterodine tartrate, Topotecan acetate, Topotecan hydrochloride, Topsentin, Topsentine B1, Trabectedin, trans-Resveratrol, Traxoprodil, Traxoprodil mesylate, Trimidox, Triphendiol, Triproamylin acetate, Troglitazone, Troxerutin, Tubastrine ((+)-enantiomer), Tubulysin A, Tubulysin B, Tubulysin C, Tucaresol, Tulobuterol-(R), Tyropeptin A10, Tyropeptin A6, Tyropeptin A9, Tyroservaltide, Tyroservatide, Tyrphostin 47, Tyrphostin A9, Tyrphostin AG-213, Uncarinic acid A, Uncarinic acid B, Uncialamycin, Valrubicin, Vancomycin hydrochloride, Vastribil, V-Echinocandin, Veinamitol, Venorphin, Verticillatine, Vesiculin, Vexibinol, V-Glycopeptide, Vialinin B, Vinaxanthone, Viniferifuran, Virgisin-1, Virgisin-2, Vitamin-P4, W Peptide, Wiedendiol A, Wiedendiol B, Woodorien, Xamoterol fumarate, Xanthoangelol E, Xanthofulvin, Xanthomegnin, Xipamide, Yatakemycin, Yttrium-90 edotreotide, Zelandopam hydrochloride, Ziconotide, Zorubicin hydrochloride.

Preferably, the carrier group Z is a polymer with a molecular weight≥500 g/mol.

In one embodiment, the carrier Z may be a PEG moiety. Such PEG moiety may be attached to the biologically active agent through one or more linkages. In case of one linkage, the corresponding PEG in the PEG prodrug monoconjugate may be linear or branched. In case of more than one linkage, such as in a bisconjugate, the corresponding PEG in the PEG prodrug may be linear or branched. Bisconjugates may contain one or two transient linkages, and PEG may be linear or branched or may contain a mixture of one linear and one branched chain. In case the bisconjugate contains one transient linkage and one linear and one branched chain the transient linkage may be on either chain. In case a branched PEG chain is used, there may be one or more branching units.

A branched PEG is a PEG molecule consisting of a branching point connecting two or more PEG chains, to form a molecule with one anchoring point for attachment to the biologically active agent. This could be two 20 kDa PEG chains joined together to form one branched 40 kDa PEG molecule. In the case where the molecule contains two or three branching points, the molecule is referred to 3- and 4-armed PEG, respectively.

In summary and within the restrictions mentioned above, the PEG polymer is not limited to a particular structure and can be linear, branched, or multi-branched.

Preferably, Z is a hydrogel and more preferably a PEG-based hydrogel. Preferably, the covalent attachment formed between the linker and the hydrogel Z is a permanent bond. The term "PEG based" as understood herein means that the mass proportion of PEG chains in the hydrogel is at least 10% by weight, preferably at least 25%, based on the total weight of the hydrogel. The remainder can be made up of spacers and/or oligomers or polymers, such as oligo- or polylysines.

Preferably, $L^1$ is substituted with one $L^2$ moiety.

Moreover, the term "water-insoluble" refers to a swellable three-dimensionally crosslinked molecular network froming the hydrogel. If suspended in a large surplus of water or aqueous buffer of physiological osmolality the hydrogel may take up a substantial amount of water, e.g. up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

According to this invention, the hydrogel may be composed of backbone moieties interconnected by hydrolytically degradable bonds.

Preferably, the backbone moiety has a molecular weight in the range of from 1 kDa to 20 kDa, more preferably from 1 kDa to 15 kDa and even more preferably from 1 kDa to 10 kDa. The backbone moieties are preferably also PEG-based, comprising one or more PEG chains.

A preferred aspect of the present invention is a carrier-linked prodrug comprising a biodegradable hydrogel as carrier, wherein a number of permanent linkages of the backbone moieties exist with the linker L to which the biologically active moiety is covalently attached.

Ideally, the hydrogel-connected drug-linker conjugates are dispersed homogeneously throughout the hydrogel according to the invention, and may or may not be present on the surface of the hydrogel according to the invention.

The functional groups may be attached to a linear chain. In this case, the functional groups may be spaced regularly or irregularly across the chain, or alternatively, the chain may be terminated by two dendritic moieties, providing for the total of functional groups.

Remaining reactive functional groups which are not connected to a transient prodrug linker or to a spacer connected to a transient prodrug linker may be capped with suitable blocking reagents.

Preferably, the covalent attachment formed between the reactive functional groups provided by the backbone moieties and the prodrug linker are permanent bonds. Suitable functional groups for attachment of the prodrug linker to the hydrogel according to the invention include but are not limited to carboxylic acid and derivatives, carbonate and derivatives, hydroxyl, hydrazine, hydroxylamine, maleamic acid and derivatives, ketone, amino, aldehyde, thiol and disulfide.

Such biodegradable hydrogel may be composed of backbone moieties interconnected by hydrolytically degradable bonds. The backbone moiety is characterized by a number of functional groups, comprising interconnected biodegradable functional groups and hydrogel-connected drug-linker conjugates, and optionally capping groups. This means that a backbone moiety is characterized by a number of hydrogel-connected drug-linker conjugates; functional groups, comprising biodegradable interconnected functional groups; and optionally capping groups. Preferably, the sum of interconnected biodegradable functional groups and drug-linker conjugates and capping groups is 16-128, preferred 20-100, more preferred 24-80 and most preferred 30-60.

Preferably, the sum of interconnected functional groups and hydrogel-connected drug-linker conjugates and capping groups of a backbone moiety is equally divided by the number of PEG-based polymeric chains extending from the branching core. For instance, if there are 32 interconnected functional groups and hydrogel-connected drug-linker conjugates and capping groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups and hydrogel-connected drug-linker conjugates and capping groups per PEG-based polymeric chain is kept to a minimum.

Preferably, a backbone moiety is further characterized by having a branching core, from which at least three PEG-based polymeric chains extend. Accordingly, in a preferred aspect the backbone reagent comprises a branching core, from which at least three PEG-based polymeric chains extend. Such branching cores may be comprised of suitably substituted derivatives of pentaerythritol, tripentaerythritol, hexaglycerine, sucrose, sorbitol, fructose, mannitol, glucose, cellulose, amylases, starches, hydroxyalkyl starches, polyvinylalcohols, dextranes, hyaluronans, or branching cores may be comprised of poly- or oligoamines such as ornithine, diaminobutyric acid, trilysine, tetralysine, pentalysine, hexylysine, heptalysine or oligolysine, nonalysine, decalysine, undecalysine, dodecalysine, tridecalysine, tetradecalysine, pentadecalysine or oligolysines, low-molecular weight PEI, polyvinylamines, low-molecular weight PEI, polyvinylamines, hexaglycerine, tripentaerythritol, in bound form.

Preferably, the branching core extends three to sixteen PEG-based polymeric chains, more preferably four to eight. Preferred branching cores may be comprised of pentaerythritol, ornithine, diaminobutyric acid, trilysine, tetralysine, pentalysine, hexylysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a linear poly(ethylene glycol) chain, of which one end is connected to the branching core and the other to a hyperbranched dendritic moiety. It is understood that a polymeric PEG-based chain may be terminated or interrupted by alkyl or aryl groups optionally substituted with heteroatoms and chemical functional groups.

Preferentially, a backbone moiety is characterized by having a branching core, from which at least three chains extend. Such branching cores may be provided by suitably substituted derivatives of poly- or oligoalcohols, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be provided by suitably substituted derivatives of poly- or oligoamines such as trilysine, tetralysine, pentalysine, hexylysine, heptalysine, octalysine, nonalysine, decalysine, undecalysine, dedecalysine, tridecalysine, tetradecalysine, pentadecalysine or oligolysines, polyethyleneimines, polyvinylamines. Preferably, the branching core extends three to sixteen chains, more preferably four to eight. Preferably, such chain is a linear polyethylene glycol chain, of which one end is connected to the branching core and the other to a hyperbranched dendritic moiety.

Preferably, a PEG-based polymeric chain is a suitably substituted poly(ethylene glycol) derivative (PEG based).

Preferred structures for corresponding PEG-based polymeric chains extending from a branching core contained in a backbone moiety are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 2.5 kDa to 15 kDa and even more preferably 5 kDa to 10 kDa. It is understood that the terminal amine groups of the above mentioned multi-arm molecules are present in bound form in the backbone moiety to provide further interconnected functional groups and reactive functional groups of a backbone moiety.

It is preferred that the sum of interconnected functional groups and reactive functional groups of a backbone moiety is equally divided by the number of PEG-based polymeric chains extending from the branching core. If the number of PEG-based polymeric chains extending from the branching core does not allow for an equal distribution, it is preferred that the deviation from the mean number of the sum of interconnected and reactive functional groups per PEG-based polymeric chain is kept to a minimum.

More preferably, the sum of interconnected and reactive functional groups of a backbone moiety is equally divided by the number of PEG-based polymeric chains extending from the branching core. For instance, if there are 32 interconnected functional groups and reactive functional groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

Such multi-arm PEG derivatives may be connected to dendritic moieties to obtain additional functional groups.

Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties are comprised of trilysine, tetralysine, pentalysine, hexylysine, heptalysine, octadecalysine, nonadecalysine in bound form. Examples for such preferred dendritic moieties are comprised of trilysine, tetralysine, pentalysine, hexylysine, heptalysine in bound bound form, most preferred trilysine, pentalysine or heptalysine. Preferably, such dendritic moieties are comprised of lysine, dilysine, trilysine, tetralysine, pentalysine, hexylysine, heptalysine, most preferred trilysine, pentalysine or heptalyine, in bound form.

Most preferably, the hydrogel of the prodrugs of the present invention is characterized in that the backbone moiety has a quarternary carbon of formula $C(A-Hyp)_4$, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four groups representing the interconnected functional groups and biodegradable and permanent linkages.

Preferably, each A is independently selected from the formula $-(CH_2)_{n1}(OCH2CH2)_nX-$, wherein n1 is 1 or 2; n is an integer in the range of from 5 to 50; and X is a functional group covalently linking A and Hyp.

Preferably, A and Hyp are covalently linked by an amide functional group.

Preferably, the dendritic moiety Hyp is a hyperbranched polypeptide. Preferably, the hyperbranched polypeptide comprises lysine in bound form, most preferably Hyp is heptalysinyl in bound form. Preferably, each dendritic moiety Hyp has a molecular weight in the range of from 0.4 kDa to 4 kDa, more preferably in the range of from 0.4 kDa to 2 kDa. It is understood that a backbone moiety $C(A-Hyp)_4$ can consist of the same or different dendritic moieties Hyp and that each Hyp can be chosen independently. Each moiety Hyp consists of between 5 and 32 lysines, preferably of at least 7 lysines, i.e. each moiety Hyp is comprised of between 5 and 32 lysines in bound form, preferably of at least 7 lysines in bound form. Most preferably Hyp is comprised of heptalysinyl.

The reaction of polymerizable functional groups a backbone reagent, more specifically of Hyp with the polymerizable functional groups of polyethyleneglycol based crosslinker reagents results in a permanent amide bond.

One preferred backbone moiety is shown below, dashed lines indicate interconnecting biodegradable linkages to crosslinker moieties and n is an integer of from 5 to 50:

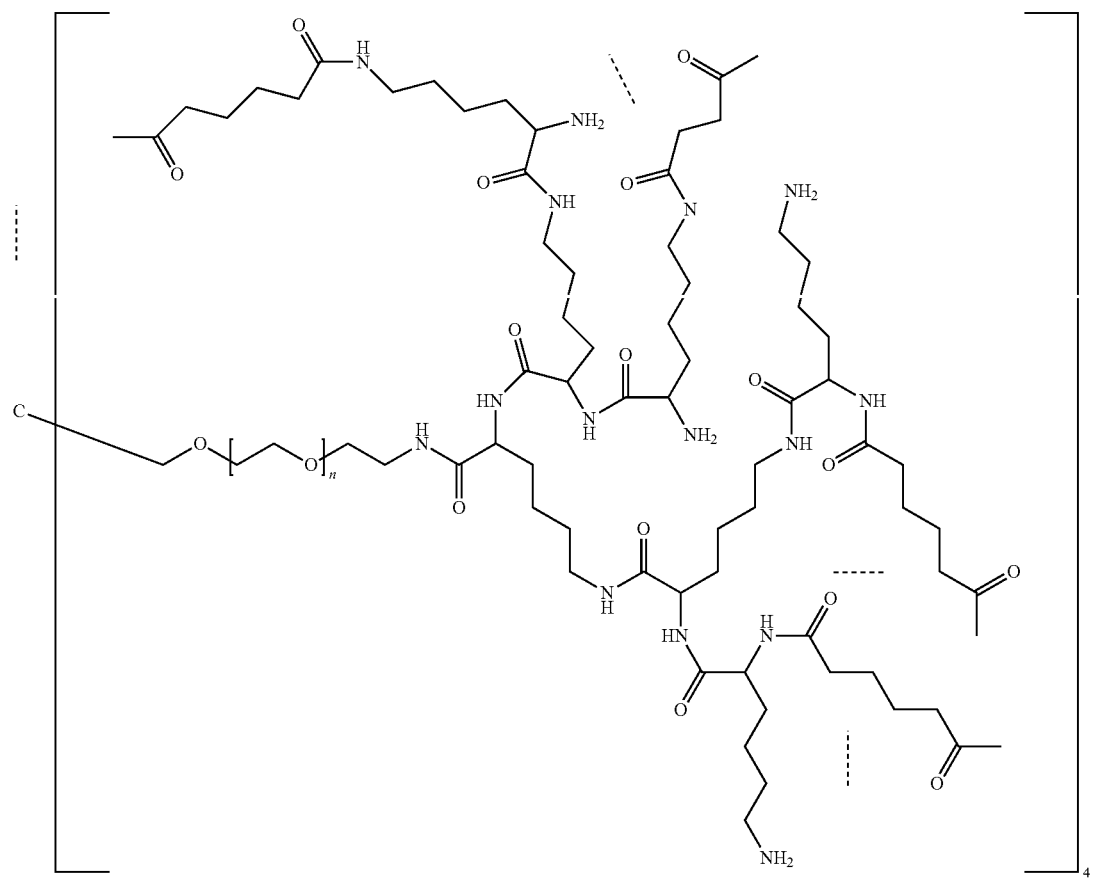

Preferably, $C(A-Hyp)_4$ has a molecular weight in the range of from 1 kDa to 20 kDa, more preferably 2.5 kDa to 15 kDa and even more preferably 5 kDa to 10 kDa.

Preferably, $L^2$ is attached to Z through a thiosuccinimide group which in turn is attached to the hydrogel's backbone moiety through a spacer, such as an oligoethylene glycol chain. Preferably, the linkage of this spacer chain to the backbone moiety is a permanent bond, preferably an amide bond.

Preferably, $L^2$ is a chemical bond.

Biodegradability of the hydrogels according to the present invention is achieved by introduction of hydrolytically degradable bonds.

The terms "hydrolytically degradable" "biodegradable" or "hydrolytically cleavable", "auto-cleavable", or "self-cleavage", "self-cleavable", "transient" or "temporary" refer within the context of the present invention to bonds and linkages which are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates. It is understood that for in vitro studies accelerated conditions like, for example, pH 9, 37° C., aqueous buffer, may be used for practical purposes.

Permanent linkages are non-enzymatically hydrolytically degradable under physiological conditions (aqueous buffer at pH 7.4, 37° C.) with half-lives of six months or longer, such as, for example, amides.

The degradation of the hydrogel is a multi-step reaction where a multitude of degradable bonds is cleaved resulting in degradation products which may be water-soluble or water-insoluble. However each water-insoluble degradation product further comprises degradable bonds so that it can be cleaved in that water-soluble degradation products are obtained. These water-soluble degradation products may comprise one or more backbone moieties. It is understood that released backbone moieties may, for instance, be permanently linked to spacer or blocking groups and/or prodrug-linker degradation products.

In such hydrogel-linked prodrugs according to the invention, it is desirable that almost all release of biologically active agent (>90%) has occurred before a significant amount of release of the backbone degradation products (<10%) has taken place. This can be achieved by adjusting the hydrogel-linked prodrug's half-life versus the hydrogel degradation kinetics.

To introduce the hydrolytically cleavable bonds into the hydrogel carrier of the invention, the backbone moieties can be directly linked to each other by means of biodegradable bonds.

In one embodiment, the backbone moieties of the biodegradable hydrogel carrier may be linked together directly, i.e. without crosslinker moieties. The hyperbranched dendritic moieties of two backbone moieties of such biodegradable hydrogel may either be directly linked through an interconnected functional group that connects the two hyperbranched dendritic moieties. Alternatively, two hyperbranched dendritic moieties of two different backbone moieties may be interconnected through two spacer moieties connected to a backbone moiety and on the other side connected to a crosslinking moiety separated by an interconnected functional group.

Preferably, backbone moieties may be linked together through crosslinker moieties, each crosslinker moiety being terminated by at least two of the hydrolytically degradable bonds. In addition to the terminating degradable bonds, the crosslinker moieties may contain further biodegradable bonds. Thus, each end of the crosslinker moiety linked to a backbone moiety shows a hydrolytically degradable bond, and additional biodegradable bonds may optionally be present in the crosslinker moiety.

The hydrogel may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

If present in a hydrogel according to the invention as degradable interconnected functional group, preferred biodegradable linkages are carboxylic esters, carboxylic anhydrides, carbonates, phosphoesters and sulfonic acid esters; more preferably carboxylic esters, carbonates, phosphoesters and sulfonic acid esters and most preferred are carboxylic esters or carbonates.

In one embodiment, a crosslinker moiety consists of a polymer. Preferably, crosslinker moieties have a molecular weight in the range of from 0.5 kDa to 5 kDa, more preferably, from 1 kDa to 4 kDa, even more preferably from 1 kDa to 3 kDa.

In addition to oligomeric or polymeric crosslinking moieties, low-molecular weight crosslinking moieties may be used, especially when hydrophilic high-molecular weight backbone moieties are used for the hydrogel formation.

Preferably, the poly(ethylene glycol) based crosslinker moieties are hydrocarbon chains comprising ethylene glycol units, optionally comprising further functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

If used in reference to a crosslinker moiety or a PEG-based polymeric chain connected to a branching core, the term "PEG-based" refers to a crosslinker moiety or PEG-based polymeric chain comprising at least 20 weight % ethylene glycol moieties.

In one embodiment, monomers constituting the polymeric crosslinker moieties are connected by biodegradable bonds. Such polymeric crosslinkers may contain up to 100 biodegradable bonds or more, depending on the molecular weight of the crosslinker moiety and the molecular weight of the monomer units. Examples for such crosslinkers are polylactic acid or polyglycolic acid based. It is understood that such polylactic acid) or poly(glycolic acid) chain may be terminated or interrupted by alkyl or aryl groups and that they may optionally be substituted with heteroatoms and chemical functional groups.

Preferably, the crosslinker moieties are PEG based, preferably represented by only one PEG based molecular chain. Preferably, the poly(ethylene glycol) based crosslinkers are hydrocarbon chains comprising ethylene glycol units, optionally comprising further functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinkers have a molecular weight in the range of from 0.5 kDa to 5 kDa.

In a preferred embodiment of the present invention the crosslinker moiety consists of a PEG chain, which is symmetrically connected through ester bonds to two alpha, omega-aliphatic dicarboxylic spacers provided by backbone moieties through permanent amide bonds.

The dicarboxylic acids of the spacer moieties connected to the backbone moiety and on the other side connected to a crosslinking moiety consists of 3 to 12 carbon atoms, most preferably between 5 and 8 carbon atoms and may be substituted at one or more carbon atom. Preferred substituents are alkyl groups, hydroxy groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

Preferably, there is a permanent amide bond between the hyperbranched dendritic moiety and the spacer moiety connected to a backbone moiety and on the other side is connected to a crosslinking moiety.

One preferred crosslinker moiety is shown below; dashed lines indicate interconnecting biodegradable linkages to backbone moieties:

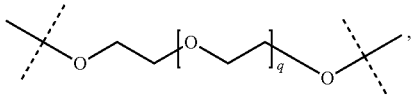

wherein q is an integer of from 5 to 50.

Preferably, the hydrogel carrier is composed of backbone moieties interconnected by hydrolytically degradable bonds.

More preferably, the backbone moieties comprise a branching core of the following formula:

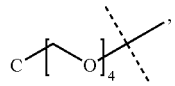

wherein the dashed line indicates attachment to the remainder of the backbone moiety.

More preferably, the backbone moieties comprise a structure of the following formula:

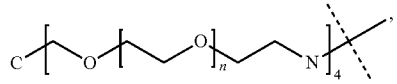

wherein n is an integer of from 5 to 50 and the dashed line indicates attachment to the remainder of the backbone moiety.

Preferably, backbone moiety comprises a hyperbranched moiety Hyp.

More preferably, the backbone moiety comprises a hyperbranched moiety Hyp of the following formula:

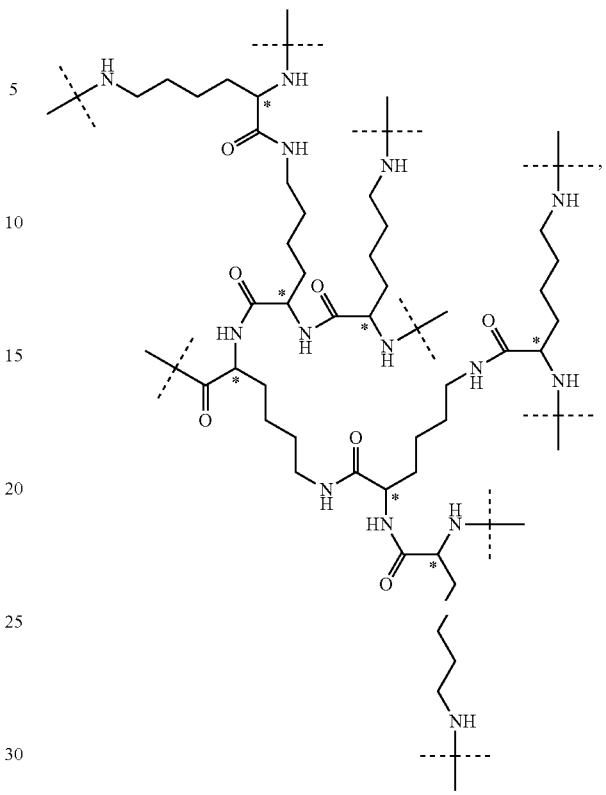

wherein the dashed lines indicate attachment to the rest of the molecule and carbon atoms marked with asterisks indicate in a preferred embodiment S-configuration. However, it is understood that hyperbranched moieties Hyp as shown above may also be in R-confirmation or may be racemic.

Preferably, the backbone moieties are attached to at least one spacer of the following formula:

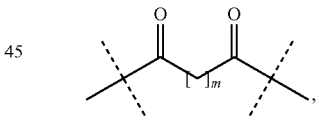

wherein one of the dashed lines indicates attachment to the hyperbranched moiety Hyp and the second dashed line indicates attachment to the rest of the molecule; and wherein m is an integer of from 2 to 4.

Preferably, the backbone moieties are linked together through crosslinker moieties having the following structure

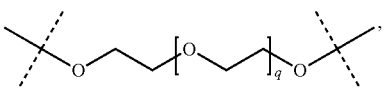

wherein q is an integer from 3 to 100.

More preferably, the backbone moieties of the hydrogel are linked together through moieties of the following formula:

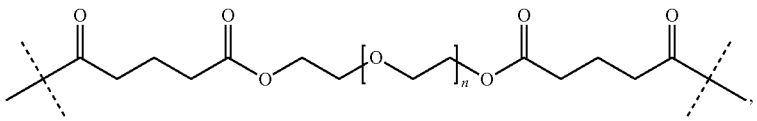

wherein the dashed lines indicate attachment to a backbone moiety, respectively, and wherein n is 45.

In an alternative preferred embodiment, the backbone moieties of the hydrogel are linked together through moieties of the following formula:

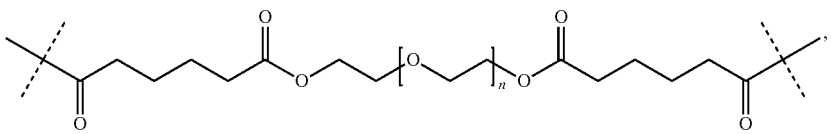

wherein the dashed lines indicate attachment to a backbone moiety, respectively, and wherein n is 22.

The hydrolysis rate of the biodegradable bonds between backbone and crosslinker moieties is influenced or determined by the number and type of connected atoms adjacent to the PEG-ester carboxy group. For instance by selecting from succinic, adipic or glutaric acid for PEG ester formation it is possible to vary the degradation half-lives of the biodegradable hydrogel carrier.

The hydrogel-linked prodrug of the present invention can be prepared starting from the hydrogel of the present invention by convenient methods known in the art. It is clear to a practitioner in the art that several routes exist. For example, the prodrug linker mentioned above to which the biologically active moiety is covalently attached can be reacted with the reactive functional groups of the hydrogel of the present invention with or with the prodrug linker already bearing the active moiety in part or as whole.

In a preferable method of preparation, the hydrogel is generated through chemical ligation reactions. The hydrogel may be formed from two macromolecular educts with complementary functionalities which undergo a reaction such as a condensation or addition. One of these starting materials is a crosslinker reagent with at least two identical functional groups and the other starting material is a homo-multifunctional backbone reagent. Suitable functional groups present on the crosslinker reagent include terminal amino, carboxylic acid and derivatives, maleimide and other alpha,beta unsaturated Michael acceptors like vinylsulfone, thiol, hydroxyl groups. Suitable functional groups present in the backbone reagent include but are not limited to amino, carboxylic acid and derivatives, maleimide and other alpha, beta unsaturated Michael acceptors like vinylsulfone, thiol, hydroxyl groups.

If the crosslinker reagent's reactive functional groups are used substoichiometrically with respect to backbone reactive functional groups, the resulting hydrogel will be a reactive hydrogel with free reactive functional groups attached to the backbone structure.

Optionally, the prodrug linker may be first conjugated to the biologically active agent and the resulting prodrug linker conjugate may then react with the hydrogel's reactive functional groups. Alternatively, after activation of one of the functional groups of the prodrug linker, the linker-hydrogel conjugate may be contacted with biologically active agent in the second reaction step and excess biologically active agent may be removed by filtration after conjugation of the biologically active agent to the hydrogel-bound prodrug linker.

A preferred process for the preparation of a prodrug according to the present invention is as follows:

A preferred starting material for the backbone reagent synthesis is a 4-arm PEG tetra amine or 8-arm PEG octa amine, with the PEG reagent having a molecular weight ranging from 2000 to 10000 Dalton, most preferably from 2000 to 5000 Da. To such multi-arm PEG-derivatives, lysine residues are coupled sequentially to form the hyperbranched backbone reagent. It is understood that the lysines can be partially or fully protected by protective groups during the coupling steps and that also the final backbone reagent may contain protective groups. A preferred building block is bis-boc lysine. Alternatively, instead of sequential additions of lysine residues, a dendritic poly-lysine moiety may be assembled first and subsequently coupled to the 4-arm PEG tetra amine or 8-arm PEG octa amine. It is desirable to obtain backbone reagent carrying 32 amino groups, consequently seven lysines would be attached to each arm of a 4-arm PEG, or three lysines would be attached to each arm of an 8-arm PEG. In another embodiment, the multi-arm PEG derivative is a tetra- or octa carboxy PEG. In this case, the dendritic moieties may be generated from glutaric or aspartic acid, and the resulting backbone reagent would carry 32 carboxy groups. It is understood that all or a fraction of the backbone reagent's functional groups may be present in a free form, as salts or conjugated to protecting groups. It is understood that due to practical reasons the backbone reagent's number of lysines per PEG-arm will be between six and seven, more preferably approximately seven.

A preferred backbone reagent is shown below:

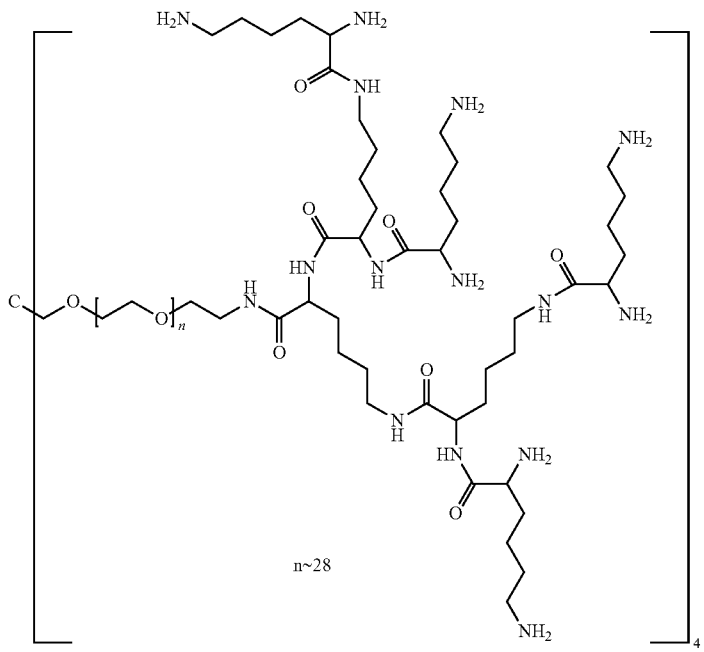

Synthesis of the crosslinker reagent starts from a linear PEG chain with a molecular weight ranging from 0.2 to 5 kDa, more preferably from 0.6 to 2 kDa, which is esterified with a half ester of a dicarboxylic acid, preferably adipic acid or glutaric acid. A preferred protecting group for half ester formation is the benzylic group. The resulting bis dicarboxylic acid PEG half esters are converted into more reactive carboxy compounds, such as acyl chlorides or active esters, e.g. pentafluorophenyl or N-hydroxysuccinimide esters, most preferred N-hydroxysuccinimde esters, of which a preferred selected structure is shown below.

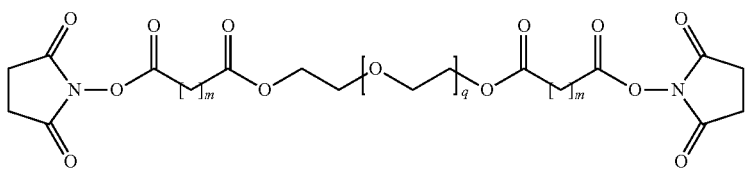

wherein each m independently is an integer ranging from 2 to 4, and
q is an integer of from 3 to 100.
More preferred is the following structure:

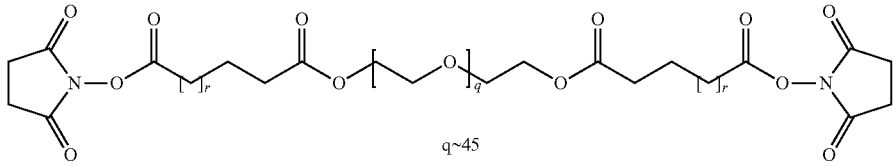

wherein r is either 1 or 2, preferably 1.
Alternatively, the bis dicarboxylic acid PEG half esters may be activated in the presence of a coupling agent such as DCC or HOBt or PyBOP.

In an alternative embodiment, the backbone reagent carries carboxy groups and the corresponding crosslinker reagent would be selected from ester-containing amino-terminated PEG-chains.

Backbone reagent and crosslinker reagent may be polymerized to form the hydrogel according to the invention using inverse emulsion polymerization. After selecting the desired stoichiometry between backbone and crosslinker functional groups, backbone and crosslinker are dissolved in DMSO and a suitable emulgator with an appropriately selected HLB value, preferably Arlacel P135, is employed to form an inverse emulsion using a mechanical stirrer and controlling the stirring speed. Polymerization is initiated by the addition of a suitable base, preferably by N,N,N',N'-tetramethylene diamine. After stirring for an appropriate amount of time, the reaction is quenched by the addition of an acid, such as acetic acid and water. The beads are harvested, washed, and fractionated according to particle size by mechanical sieving. Optionally, protecting groups may be removed at this stage.

In an alternative embodiment of this invention, multifunctional moieties are coupled to the reactive functional groups of the polymerized reactive hydrogel to increase the number of functional groups which allows increasing the drug load of the hydrogel. Such multi-functional moieties may be provided by suitably substituted derivatives of lysine, dilysine, trilysine, tetralysine, pentalysine, hexylysine, heptalysine, or oligolysine, low-molecular weight PEI. Preferably, the multi-functional moiety is lysine.

Further, such hydrogel according to the invention may be functionalized with a spacer carrying a different reactive functional group than provided by the hydrogel. For instance maleimide reactive functional groups may be introduced into the hydrogel by coupling a suitable heterobifunctional spacer such as Mal-PEG6-NHS to the hydrogel. Such functionalized hydrogel can be further conjugated to drug-linker reagents, carrying a reactive thiol group on the linker moiety to form hydrogel-linked prodrugs according to the present invention.

After loading the drug-linker conjugate to the functionalized maleimido group-containing hydrogel, all remaining functional groups are capped with a suitable blocking reagent, such as mercaptoethanol, to prevent undesired side-reactions.

A particularly preferred method for the preparation of a prodrug of the present invention comprises the steps of
  (a) reacting a compound of formula $C(A'-X1)_4$, wherein A'-X1 represents A before its binding to Hyp or a precursor of Hyp and X1 is a suitable functional group, with a compound of formula Hyp'-X2, wherein Hyp'-X2 represents Hyp before its binding to A or a precursor of Hyp and X2 is a suitable functional group to react with X1;
  (b) optionally reacting the resulting compound from step (a) in one or more further steps to yield a compound of formula $C(A-Hyp)_4$ having at least four functional groups;
  (c) reacting the at least four functional groups of the resulting compound from step (b) with a poly(ethylene glycol) based crosslinker precursor, wherein the crosslinker precursor is used in a sub-stoichiometric amount compared to the total number of functional groups of $C(A-Hyp)_4$ to yield a hydrogel;
  (d) reacting remaining un-reacted functional groups (representing the reactive functional groups of the backbone comprised in the hydrogel) in the hydrogel backbone of step (c) with a covalent conjugate of biologically active moiety and transient prodrug linker or first reacting the un-reacted functional groups with the transient prodrug linker and subsequently with the biologically active moiety;
  (e) optionally capping remaining un-reacted functional groups to yield a prodrug of the present invention.

Such hydrogel is preferably comminuted by mechanical processes such as stirring, crushing, cutting pressing, or milling, and optionally sieving. For emulsion polymerization, the reaction mixture is comprised of the dispersed phase and the continuous phase.

For the dispersed phase, backbone reagent and crosslinker reagent are mixed in a ratio amine/active ester of 5:1 to 1.05:1, preferably of 2:1 to 1.05:1 and are dissolved in DMSO to give a to give a solution with a concentration of 5 to 50 g per 100 mL, preferably 7 to 30 g per 100 ml, more preferably 7.5 to 20 g per 100 ml and most preferably 10 to 20 g per 100 ml.

The continuous phase is any solvent, that is not miscible with DMSO, not basic, aprotic and shows a viscosity lower than 10 Pa*s. Preferably, the solvent is not miscible with DMSO, not basic, aprotic, shows a viscosity lower than 2 Pa*s and is non-toxic. More preferably, the solvent is a saturated linear or branched hydrocarbon with 5 to 10 carbon atoms. Most preferably, the solvent is n-heptane.

To form an emulsion of the dispersed phase in the continuous phase, an emulsifier is added to the continuous phase before adding the dispersed phase. The amount of emulsifier is 2 to 50 mg per mL dispersed phase, more preferably 5 to 20 mg per mL dispersed phase, most preferably 10 mg per mL dispersed phase.

The emulsifier has an HLB-value of 3 to 8. Preferably, the emulsifier is a triester of sorbitol and a fatty acid or an poly(hydroxyl fatty acid)-poly(ethylene glycol) conjugate. More preferably, the emulsifier is an poly(hydroxy-fatty acid)-polyethylene glycol conjugate, with a linear poly(ethylene glycol) of a molecular weight in the range of from 0.5 kDa to 5 kDa and poly(hydroxy-fatty acid) units of a molecular weight in the range of from 0.5 kDa to 3 kDa on each end of the chain. Most preferably, the emulsifier is poly(ethylene glycol) dipolyhydroxy stearate, Cithrol DPHS (Cithrol DPHS, former Arlacel P135, Croda International Plc).

Droplets of the dispersed phase are generated by stirring with an axial flow impeller with a geometry similar to stirrers such as Isojet, Intermig, Propeller (EKATO Ruhr- and Mischtechnik GmbH, Germany), most preferably similar to Isojet or Propeller with a diameter of 50 to 90% of the reactor diameter. Preferably, stirring is initated before addition of the dispersed phase. Stirrer speed is set to 0.6 to 2.4 m/s, such as 0.8 to 2.3 m/s, preferably to 0.6 to 1.7 m/s. The dispersed phase is added at room temperature, and the concentration of the disperse phase is 2% to 70%, preferably 5 to 50%, more preferably 10 to 40%, and most preferably 20 to 35% of the total reaction volume. The mixture of dispersed phase, emulsifier and continuous phase is stirred for 5 to 60 min before adding the base to the effect polymerization.

5 to 10 equivalents (referred to each amide bond to be formed) of a base are added to the mixture of dispersed and continuous phase. The base is aprotic, non nucleophilic and soluble in the disperse phase. Preferably, the base is aprotic, non nucleophilic, well soluble in both disperse phase and DMSO. More preferably, the base is aprotic, non nucleophilic, well soluble in both disperse phase and DMSO, an amine base and non-toxic. Most preferably, the base is N,N,N',N'-tertramethylethylene diamine (TMEDA). Stirring in the presence of base is continued for 1 to 16 h.

During stirring, droplets of dispersed phase are hardened to become crosslinked hydrogel beads according to the invention which can be collected and fractionation according to size is performed on a vibrational continuous sieving machine with a 75 µm and a 32 µm deck to give hydrogel microparticles according to the invention.

The hydrogel for the prodrug of the present invention can be obtained from the preparation methods in form of microparticles. In a preferred embodiment of the invention, the reactive hydrogel is a shaped article such as a mesh or a stent. Most preferably, the hydrogel is formed into microparticulate beads which can be administered as subcutaneous or intramuscular injectably by means of a standard syringe. Such soft beads may have a diameter of between 1 and 500 micrometer.

Preferably, such beaded carrier-linked hydrogel prodrugs have a diameter of between 10 and 100 micrometer if suspended in an isotonic aqueous formulation buffer, most preferably a diameter of between 20 and 100 micrometer, most preferably a diameter of between 25 and 80 micrometer.

Preferably, such beaded carrier-linked hydrogel prodrugs can be administered by injection through a needle smaller than 0.6 mm inner diameter, preferably through a needle smaller than 0.3 mm inner diameter, more preferably through a needle small than 0.25 mm inner diameter, even more preferably through a needle smaller than 0.2 mm inner diameter, and most preferably through a needle small than 0.16 mm inner diameter.

It is understood that the terms "can be administered by injection", "injectable" or "injectability" refer to a combination of factors such as a certain force applied to a plunger of a syringe containing the carrier-linked hydrogel prodrugs according to the invention swollen in a liquid at a certain concentration (w/v) and at a certain temperature, a needle of a given inner diameter connected to the outlet of such syringe, and the time required to extrude a certain volume of the carrier-linked hydrogel prodrugs according to the invention from the syringe through the needle.

In order to provide for injectability, a volume of 1 mL of the carrier-linked hydrogel prodrugs swollen in water to a concentration of at least 5% (w/v) and contained in a syringe holding a plunger of a diameter of 4.7 mm can be extruded at room temperature within 10 seconds by applying a force of less than 60 Newton, such as less than 50 Newton, preferably by applying a force of less than 40 Newton.

Preferably injectability measurement is carried out for the carrier-linked hydrogel prodrugs of the present invention swollen in water to a concentration of ca. 15% (w/v).

By consequence, the prodrugs according to the present invention show the beneficial effect of a controlled release rate in respect of the released drug D-H. Preferably, a sustained release rate is obtained. Sustained release means that the administration intervals of the respective prodrug are expanded. For example, prodrugs according to the present invention which are based on drugs commonly applied once or several times a day provide therapeutically effective levels for at least three days, more preferably for at least one week and even more preferably for at least one month.

The prodrug according to the present invention show excellent in vivo/in vitro correlation of linker cleavage, a high degree of enzyme independence and show a higher stability at lower pH, resulting in a pH dependent cleavage.

A strong in vivo/in vitro correlation is observed, if the release kinetics exhibited by a carrier-linked prodrug conjugate according to the invention in vivo has a half-life that is not smaller than half the value exhibited by the same carrier-linked prodrug conjugate in aqueous buffer of pH 7.4 at 37° C., wherein the release kinetics in vivo is measured as plasma levels of free drug. It is understood that in the case of soluble carriers, release kinetics may be recorded as hydrolysis kinetics.

Another aspect of the present invention are pharmaceutical compositions of the carrier-linked prodrugs described before. Such pharmaceutical compositions contain one or more excipients, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.

(iii) Preservatives and/or antimicrobials: multidose parenteral preparations may require the addition of preservatives at a sufficient concentration to minimize the risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

(iv) Stabilizers: Stabilisation is achieved by strengthening of the protein-stabilising forces, by destabilisation of the denatured stater, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used.

(v) Anti-adsorption agents: Mainly ionic or iron-ionic surfactants or other proteins or soluble polymers are used to coat or adsorb competitively to the inner surface of the composition's container, e.g. poloxamer (Pluronic®F-68), PEG dodecyl ether (Brij 35), polysorbate 20 and 80, dextran, poly(ethylene glycol), PEG-polyhistidine, BSA and HSA and gelatines. Chosen concentration and type of excipient depends on the effect to be avoided but typically a monolayer of surfactant is formed at the interface just above the CMC value.

(vi) Lyo- and/or cryoprotectants: During freeze- or spray drying, excipients may counteract the destabilising effects caused by hydrogen bond breaking and water removal. For this purpose, sugars and polyols may be used, but corresponding positive effects have also been observed for surfactants, amino acids, non-aqueous solvents, and other peptides. Trehalose is particulary efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol may be used as the sole protectant. Starch or starch derivatives may also be used.

(vii) Oxidation protection agents: antioxidants such as ascorbic acid, ectoine, methionine, glutathione, monothioglycerol, morin, polyethylenimine (PEI), propyl gallate, vitamin E, chelating agents such aus citric acid, EDTA, hexaphosphate, thioglycolic acid.

(viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly (glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a poly(ethylene glycol) terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as poly(ethylene glycol) (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(ix) Spreading or diffusing agent: modifies the permeability of connective tissue through the hydrolysis of components of the extracellular matrix in the intrastitial space such as, but not limited to, hyaluronic acid, a polysaccharide found in the intercellular space of connective tissue. A spreading agent such as, but not limited to, hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

The composition of a prodrug according to the invention may be provided as a liquid composition, a suspension composition or as a dry composition.

In one embodiment, the pharmaceutical composition of a prodrug according to the invention is a dry composition. Suitable methods of drying are, for example, spray-drying and lyophilization (freeze-drying). Preferably, the pharmaceutical composition of prodrug is dried by lyophilization.

Preferably, the prodrug is sufficiently dosed in the composition to provide therapeutically effective amounts of biologically active agent for at least 12 hours in one application. More preferably, one application of prodrug is sufficient for at least one day, more preferably for at least 3 days, more preferably for at least 1 week and most preferably for at least 4 weeks.

In one embodiment of the present invention, the composition of prodrug is provided as a single dose, meaning that the container in which it is supplied contains one pharmaceutical dose.

In another embodiment, the composition is provided as a multiple dose composition, meaning that it contains more than one therapeutic dose. Preferably, a multiple dose composition contains at least 2 doses. Such multiple dose composition of prodrug can either be used for different patients in need thereof or is intendend for use in one patient, wherein the remaining doses are stored after the application of the first dose until needed.

In another aspect of the present invention the prodrug composition is comprised in a container. For liquid or suspension compositions, the container is preferably a single chamber syringe. For dry compositions, preferably the container is a dual-chamber syringe. The dry composition according to the present invention is provided in a first chamber of the dual-chamber syringe and reconstitution solution is provided in a second chamber of the dual-chamber syringe.

Prior to applying the dry composition of prodrug to a patient in need thereof, the dry composition is reconstituted. Reconstitution can take place in the container in which the dry composition of prodrug is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials, such as, for example, benzylalcohol and cresol. Preferably, the reconstitution solution is sterile water.

A further aspect is a method of preparing a reconstituted composition comprising a therapeutically effective amount of prodrug, and optionally one or more pharmaceutically acceptable excipients, the method comprising the step of
    contacting the composition of the present invention with a reconstitution solution.

Another aspect is a reconstituted composition comprising a therapeutically effective amount of a prodrug according to the invention, and optionally one or more pharmaceutically acceptable excipients.

Another aspect of the present invention is the method of manufacturing a liquid or suspension composition of carrier-linked prodrug. In one embodiment, such composition is made by
    (i) admixing the carrier-linked prodrug with one or more excipients,
    (ii) transferring amounts of the liquid or suspension composition equivalent to single or multiple doses into suitable containers, and
    (iii) sealing the containers.

Another aspect of the present invention is the method of manufacturing a dry composition of carrier-linked prodrug. In one embodiment, such composition is made by
    (i) admixing the carrier-linked prodrug with one or more excipients,
    (ii) transferring amounts equivalent to single or multiple doses into suitable containers,
    (iii) drying the composition in said containers, and
    (iv) sealing the containers.

Suitable containers are vials, syringes, dual-chamber syringes, ampoules, and cartridges.

Another aspect is a kit of parts. For liquid and suspension compositions, and when the administration device is simply a hypodermic syringe, the kit may comprise the syringe, a needle and a container comprising the carrier-linked prodrug composition for use with the syringe. In case of a dry composition, the container may have one chamber containing the dry carrier-linked prodrug composition, and a second chamber comprising a reconstitution solution. In more preferred embodiments, the injection device is other than a simple hypodermic syringe and so the separate container with carrier-linked prodrug composition is adapted to engage with the injection device such that in use the liquid or suspension or reconstituted dry composition in the container is in fluid connection with the outlet of the injection device. Examples of administration devices include but are not limited to hypodermic syringes and pen injector devices. Particularly preferred injection devices are the pen injectors, in which case the container is a cartridge, preferably a disposable cartridge.

A preferred kit of parts comprises a needle and a container containing the dry carrier-linked prodrug composition according to the present invention and optionally further containing a reconstitution solution, the container being adapted for use with the needle. Preferably, the container is a dual-chamber syringe.

In another aspect, the invention provides a cartridge containing a composition of carrier-linked prodrug as hereinbefore described for use with a pen injector device. The cartridge may contain a single dose or multiplicity of doses of carrier-linked prodrug.

In one embodiment of the present invention the suspension composition of carrier-linked prodrug does not only comprise a carrier-linked prodrug and one or more excipients, but also other biologically active agents, either in their free form or as prodrugs or carrier-linked prodrugs such as PEG prodrugs or hydrogel prodrugs. Preferably, such additional one or more biologically active agent is a prodrug, more preferably a PEG or hydrogel prodrug.

In an alternative embodiment, the carrier-linked prodrug composition according to the present invention is combined with a second biologically active compound in such way that the carrier-linked prodrug composition according to the invention is administered to a patient in need thereof first, followed by the administration of the second compound. Alternatively, the carrier-linked prodrug composition is administered to a patient in need thereof after another compound has been administered to the same patient.

Another subject of the present invention is the use of prodrugs or a pharmaceutically acceptable salt thereof comprising a drug linker conjugate D-L as pharmaceuticals or medicaments, respectively. With respect of the definitions of the drug linker conjugate D-L as well as further substituents such as $L^1$ the same explanations as laid out above in the context of the prodrug as such apply.

Yet another aspect of the present invention is a carrier-linked prodrug of the present invention or a pharmaceutical composition of the present invention for use in a method of treating or preventing diseases or disorders which can be treated by the biologically active moiety released from the carrier-linked prodrug according to the present invention.

Another subject of the present invention is a pharmaceutical composition comprising an effective dose of at least one prodrug or a pharmaceutically acceptable salt thereof as defined above and a pharmaceutically acceptable excipient.

Furthermore, the present invention also comprises the use of such pharmaceutical compositions as pharmaceuticals or medicaments, respectively.

Another subject of the present invention is a method for the synthesis of a prodrug or a pharmaceutically acceptable salt thereof as defined above. Prodrugs or precursors of prodrugs according to the present invention may be prepared by known methods or in accordance with the reaction sequences described below. The starting materials used in the preparation (synthesis) of prodrugs of the invention or precursors thereof are known or commercially available, or can be prepared by known methods or as described below.

All reactions for the synthesis of the prodrugs according to the present invention including precursors such as the moiety $L^1$ according to the formula (I) are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a prodrug or a precursor thereof, it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the prodrugs or precursors can be purified by customary purification procedures, for example by recrystallization or chromatography.

The prodrugs according to the present invention (or a pharmaceutically acceptable salt thereof) may be prepared by a method comprising the step of reacting a prodrug precursor L-Y with a biologically active drug D-H to obtain the drug linker conjugate D-L by forming an carbamate bond, wherein Y is a leaving group.

In respect of the prodrug precursor L-Y, L has the same meaning as indicated above in connection with the drug linker conjugate D-L. The same holds true for the analogous employment of the prodrug precursor L1-Y in respect of the moiety L1 represented by formula (I).

Y is a leaving group. Such leaving groups are known to a person skilled in the art. Preferably, Y is chloride, bromide, fluoride, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, or N-hydroxysulfosuccinimidyl.

In case the synthesis of a carrier-linked prodrug according to the present invention is carried out by employing a precursor $L^1$-Y, a drug linker intermediate ($L^1$-D) is obtained by reacting $L^1$-Y with the biologically active drug D-H by forming a carbamate bond. In such case, said drug linker intermediate $L^1$-D is reacted further to obtain the drug linker conjugate D-L by adding the moiety $L^2$ and the carrier group Z to said drug linker intermediate $L^1$-D. It has to be indicated that the addition of $L^2$ and/or Z to $L^1$-D may be performed in several steps by preparing further intermediate compounds prior to obtaining the drug linker conjugate D-L.

Alternatively, a prodrug precursor L*-Y may be employed instead of $L^1$-Y, wherein L* is selected from a fragment of L¹, L¹ containing at least one protecting group or L¹ additionally containing precursors of L² and/or Z.

EXAMPLES

Example 1

Synthesis of Paracetamol-Linker Conjugate 1

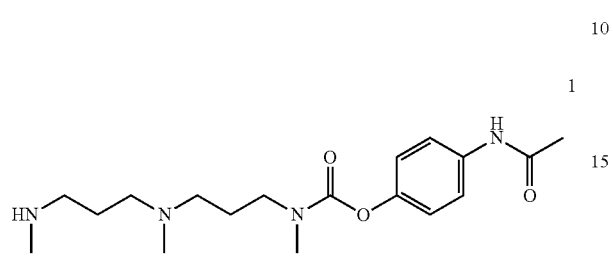

Paracetamol (1 mmol) was dissolved in 10 ml of THF and nitrophenyl-chloroformate (1.1 mmol) and DIPEA (1.1 mmol) were added. After 30 min, N,N-bis[3-(methylamino)propyl]methylamine (2 mmol) was added and reaction mixture was stirred at room temperature for 30 min. 1 was purified by RP-HPLC.

Yield 83 mg (14%).
MS: m/z=351.26 [M+H]⁺.

Example 2

Synthesis of PEG-Linker-Paracetamol Conjugate 3

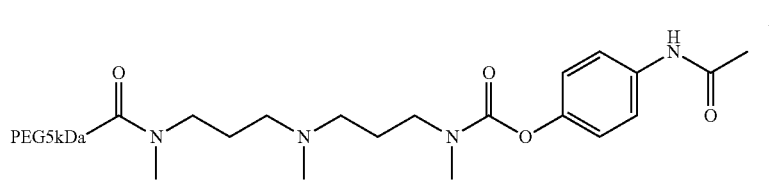

1 (31 µmol) was dissolved in DMSO (250 µL). 5 kDa methoxy poly(ethylene glycol) carboxylic acid NHS ester (15 µmol) was dissolved in DMSO (480 µL) and added to the solution of the amine. DIPEA (124 µmol) was added and the mixture solution was stirred at room temperature for 30 min. 2 was purified by RP-HPLC.

Yield 30 mg (41%).

Example 3

Release of Paracetamol In Vitro 2 was dissolved in 60 mM sodium phosphate, pH 7.4, and incubated at 37° C. Aliquots were analyzed by RP-HPLC at 242 nm and MS for released paracetamol. MS showed release of unmodified paracetamol.

$t_{1/2}$=28.8 d.

Example 4

Synthesis of Paracetamol Linker Conjugate 4

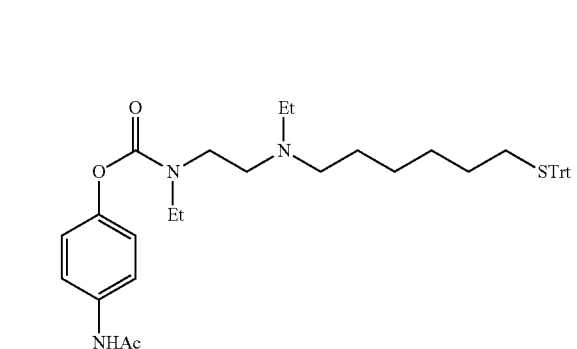

Synthesis scheme:

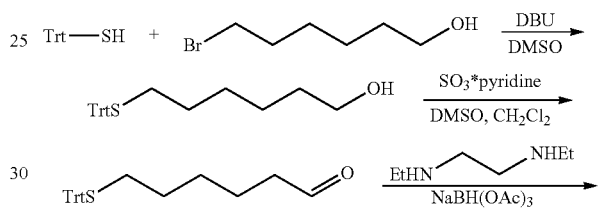

-continued

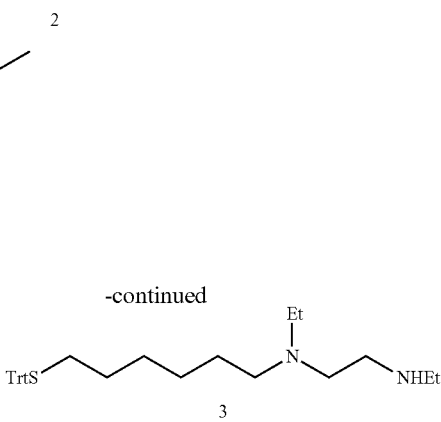

Triphenylmethane thiol (247 mg, 0.89 mmol) was suspended in DMSO (1 mL) and DBU (152 µL, 1.02 mmol) was added. After stirring at room temperature for 5 min, 4-Bromohexanol (173 mg, 0.96 mmol) was added, and the mixture was stirred for 10 min. The reaction mixture was diluted with ethyl acetate, quenched with 0.1 M HCl and extracted with ethyl acetate. The crude product was purified by flash chromatography.

Yield 283 mg (85%).
MS: m/z=375.17 [M+H]⁺.

6-Triphenylmercapto-hexane-1-ol (466 mg, 1.24 mmol) and triethylamine (600 µL, 4.34 mmol) were dissolved in dichloromethane (3.5 mL) and DMSO (500 µL), cooled to 0° C. and added to a 0° C. suspension of sulfur trioxide pyridine complex (408 mg, 2.57 mmol) in DMSO (400 µL).

The mixture was stirred for 20 min. The mixture was diluted with dichloromethane, quenched with 0.1 m HCl and brine and extracted with dichloromethane. The crude product was purified by flash chromatography.

Yield 329 mg (71%).

MS: m/z=397 [M+Na]$^+$.

To a 0° C. solution of 6-triphenylmercapto hexanal (329 mg, 0.88 mmol), N,N'-diethyl ethylene diamine (630 μL, 4.4 mmol) and acetic acid (700 μL, 12.3 mmol) in dichloromethane (5.5 mL) was added sodium triacetoxy borohydride (556 mg, 2.64 mmol), and the mixture was allowed to warm to room temperature over the course of 45 min. The mixture was diluted with dichloromethane and washed with aqueous NaOH and brine. The crude product was purified by RP-HPLC.

Yield 141 mg (34%).

MS: m/z=475.33 [M+H]$^+$.

To a solution of paracetamol (24 mg, 0.16 mmol) in tetrahydrofurane (1 mL) were added p-nitrophenyl chloroformate (35 mg, 0.17 mmol) and DIPEA (68 μL, 0.39 mmol), and the mixture was stirred at room temperature for 2 h. A solution of amine 3 (70 mg, 0.10 mmol) and DIPEA (40 μL, 0.23 mmol) in tetrahydrofurane (0.5 mL) was added, and after 1 h the reaction mixture was quenched with acetic acid. The crude product was purified by RP-HPLC.

Yield 38 mg (50%).

MS: m/z=652.36 [M+H]$^+$.

Example 5

Synthesis of PEG-Linker-Paracetamol Conjugate 6

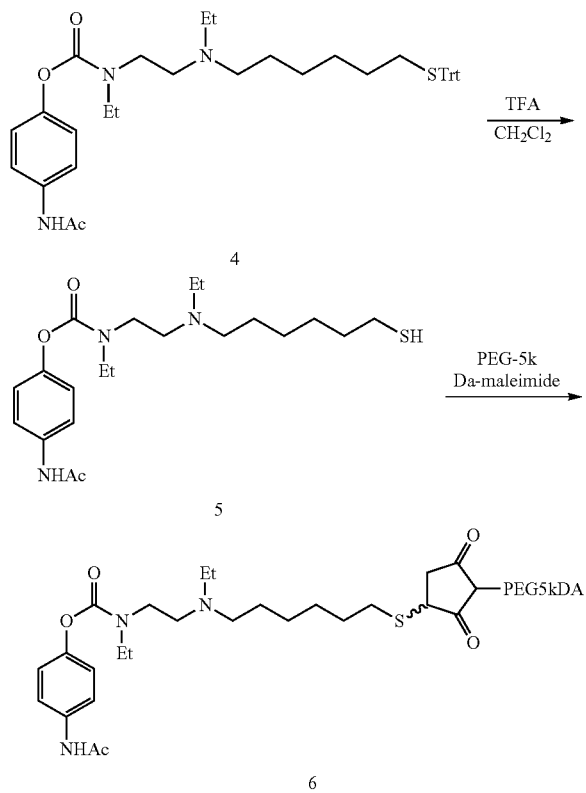

At 0° C., solid 4 (38 mg, 50 μmol) was treated with a solution of trifluoro acetic acid in dichloromethane (1:1, v/v, 2 mL). After 1 min, triethyl silane (100 μL) was added, and the reaction mixture was quenched with water after 15 min. The crude product was purified by PR-HPLC.

Yield 22 mg (84%).

MS: m/z=410.25 [M+H]$^+$.

Linker thiol 5 (5 mg, 10 dissolved in 338 μL MeCN/water 9:1 v/v, 0.05% TFA) was added to a solution of 5 kDa methoxy poly(ethylene glycol) maleimide (73 mg, 14.6 μmol) in MeCN/water 1:1 (v/v, 2 mL). phosphate buffer (0.5 M, pH7.40, 200 μL) was added, and the mixture was incubated at room temperature for 15 min. The reaction mixture was quenched with acetic acid and the crude product was purified by RP-HPLC.

Yield 6.3 mg (8%).

Example 6

Release of Paracetamol In Vitro 6 was dissolved in 60 mM sodium phosphate, pH 7.4, and incubated at 37° C. Aliquots were analyzed by RP-HPLC at 242 nm and MS for released paracetamol. MS showed release of unmodified paracetamol.

$t_{1/2}$=2.1d.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

ABBREVIATIONS d days
DBU 1,3-diazabicyclo[5.4.0]undecene
DIEPA diisopropylethylamine
DMSO dimethylsulfoxide
Et ethyl
MeCN acetonitrile
MS mass spectrometry
NHS N-hydroxy succinimide
PEG poly(ethylene glycol)
RP-HPLC reversed-phase high performance liquid chromatography
$t_{1/2}$ half-life
TFA trifluoro acetic acid
THF tetrahydrofuran
Trt triphenylmethyl, trityl

The invention claimed is:

1. A prodrug or a pharmaceutically acceptable salt thereof comprising:
    a drug linker conjugate D-L;
    wherein D is a biologically active moiety containing an aromatic hydroxyl group; and
    wherein L is a non-biologically active linker having a first and a second amine group, wherein:
        the first amine group is a primary, secondary, or tertiary amine, or a quaternary ammonium cation; and
        L is connected to D through a carbamate bond connecting the second amine group and the aromatic hydroxyl group of D;

wherein L comprises:
i) a moiety $L^1$ of formula (I);

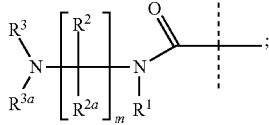

wherein the dashed line indicates the attachment of $L^1$ to the aromatic hydroxyl group of D by forming a carbamate group;
wherein $R^1$ is selected from the group consisting of:
$C_{1-4}$ alkyl;
heteroalkyl;
$C_{3-7}$ cycloalkyl; and

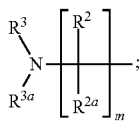

wherein $R^2$, $R^{2a}$, $R^3$, and $R^{3a}$ are independently selected from hydrogen, substituted or non-substituted linear, branched or cyclic $C_{1-4}$ alkyl, and heteroalkyl; and
wherein m is independently 2, 3 or 4; and
ii) a moiety $L^2$, which is a chemical bond or a spacer, wherein:
$L^2$ is bound to a carrier group Z; and
Z is a polymer with a molecular weight ≥500 g/mol selected from the group consisting of:
2-methacryloyl-oxyethyl phosphoyl cholins, hydrogels, PEG based hydrogels, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, mannans, pectins, rhamnogalacturonans, starches, hydroxyalkyl starches, hydroxyethyl starches and other carbohydrate-based polymers, xylans, and copolymers thereof;
wherein $L^1$ is substituted with one to four $L^2$ moieties, by replacing any one to four hydrogen(s) of $L^1$ with a moiety $L^2$; and
wherein optionally, L is further substituted.

2. The prodrug according to claim 1;
wherein $L^2$ is a chemical bond.

3. The prodrug according to claim 1;
wherein the carrier group Z is a hydrogel.

4. The prodrug of claim 3;
wherein the hydrogel is composed of backbone moieties interconnected by hydrolytically degradable bonds.

5. The prodrug of claim 4;
wherein the backbone moieties have a molecular weight in the range of from 1 kDa to 20 kDa.

6. The prodrug of claim 4;
wherein backbone moieties are linked together through crosslinker moieties, each crosslinker moiety being terminated by at least two of the hydrolytically degradable bonds.

7. The prodrug of claim 6;
wherein the crosslinker moieties have a molecular weight in the range of from 0.5 kDa to 5 kDa.

8. A pharmaceutical composition comprising:
a prodrug of claim 1 or a pharmaceutically acceptable salt thereof; and
a pharmaceutically acceptable excipient.

9. A pharmaceutical composition according to claim 8;
wherein the pharmaceutical composition is dry.

10. A pharmaceutical composition according to claim 8;
wherein the prodrug is sufficiently dosed in the composition to provide a therapeutically effective amount of biologically active agent for at least 12 hours in one application.

11. A kit of parts comprising:
a needle; and
a container containing:
reconstitution solution; and
the dry composition according to claim 10 configured for use with the needle.

12. The kit of parts according to claim 11;
wherein the container is a dual-chamber syringe; and
wherein one of the two chambers of the dual-chamber syringe contains the dry pharmaceutical composition and the second chamber of said dual-chamber syringe contains the reconstitution solution.

13. The prodrug according to claim 1;
wherein the prodrug is configured for use as pharmaceutical.

14. A method for the synthesis of a prodrug or a pharmaceutically acceptable salt thereof according to claim 1, comprising:
a step of reacting a prodrug precursor L-Y or $L^1$-Y with a biologically active drug D-H, to obtain the drug linker conjugate D-L or a drug linker intermediate D-$L^1$ by forming a carbamate bond;
wherein Y is a leaving group.

15. The prodrug according to claim 1;
wherein the carrier group Z is a PEG based hydrogel.

16. The prodrug according to claim 1;
wherein the carrier group Z is a biodegradable poly(ethylene glycol) based water-insoluble hydrogel.

* * * * *